United States Patent

Inoue et al.

[11] Patent Number: 5,935,959
[45] Date of Patent: Aug. 10, 1999

[54] PIPERAZINE DERIVATIVES AND USE AS CYSTEINE INHIBITORS

[75] Inventors: Jun Inoue, Kobe; Yuka Yoshida, Nishiwaki; Ying-She Cui, Minoo; Mitsuyoshi Azuma, Nishinomiya, all of Japan

[73] Assignee: Senju Pharmaceutical Co., Ltd., Osaka, Japan

[21] Appl. No.: 08/983,034

[22] PCT Filed: Jul. 4, 1996

[86] PCT No.: PCT/JP96/01884

§ 371 Date: Jan. 7, 1998

§ 102(e) Date: Jan. 7, 1998

[87] PCT Pub. No.: WO97/03060

PCT Pub. Date: Jan. 30, 1997

[30] Foreign Application Priority Data

Jul. 13, 1995 [JP] Japan ................................. 7-176975

[51] Int. Cl.[6] ...................... A61K 31/495; C07D 405/06; C07D 405/14
[52] U.S. Cl. ......................... 514/252; 544/372; 544/374
[58] Field of Search .................... 544/374, 372; 514/252

[56] References Cited

U.S. PATENT DOCUMENTS

| | | | |
|---|---|---|---|
| 4,507,297 | 3/1985 | Masaki et al. | 514/252 |
| 5,556,853 | 9/1996 | Tsubotani et al. | 544/374 |

FOREIGN PATENT DOCUMENTS

| | | |
|---|---|---|
| 0655447 | 5/1995 | European Pat. Off. . |
| 0771565 | 5/1997 | European Pat. Off. . |
| 275575 | 11/1988 | Japan . |
| 275576 | 11/1988 | Japan . |

OTHER PUBLICATIONS

Abstract for JP63/275575 (Nov. 14, 1988), Mazaki.
Abstract for JP63/275576 (Nov. 14, 1988), Mazaki.

*Primary Examiner*—Emily Bernhardt

*Attorney, Agent, or Firm*—Wenderoth, Lind & Ponack, L.L.P

[57] ABSTRACT

The present invention is directed to a compound of the following formula (I) inclusive of its salt

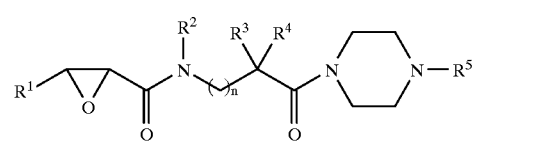

(I)

[wherein $R^1$ represents either carboxy which may be esterified or amidated carboxy which may be substituted; $R^2$ represents hydrogen or lower alkyl and may be linked to $R^3$ or $R^4$ to form a ring; $R^3$ and $R^4$ may be the same or different and each represents hydrogen, lower alkyl which may be substituted, or a sulfide group which may be substituted, and $R^3$ and $R^4$ may conjoinedly form a ring; $R^5$ represents a substituted phenyl group of formula (II)

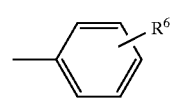

(II)

(wherein $R^6$ represents halogen or alkoxy) or a substituted sulfonyl group of formula (III)

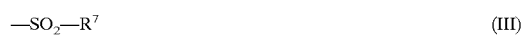

$$-SO_2-R^7$$ (III)

(wherein $R^7$ represents either aryl which may be substituted by lower alkyl or amino which may be substituted); n is to 0 or 1] and to a method for producing the same compound, which is useful for the treatment of cysteine protease-associated diseases.

9 Claims, No Drawings

PIPERAZINE DERIVATIVES AND USE AS CYSTEINE INHIBITORS

TECHNICAL FIELD

The present invention relates to a cysteine protease inhibitor composition comprising a piperazine derivative or a salt thereof as an active ingredient.

BACKGROUND TECHNOLOGY

Cysteine protease is a protease having a cysteine residue in the activity center of the enzyme molecule and includes such species as cathepsin B, H, and L and dipeptidyl peptidase, all of which are lysosomal enzyme fractions, and calpain which exists in the cytoplasm, among others. Though much remains to be explored about the physiological roles of these enzymes, a considerable amount of work has been done on their roles in recent years. For example, calpain is known to be a protease ubiquitous in life, which is activated by calcium ions and has the optimum pH in the neighborhood of neutral. As elucidated to this day, it takes part in degradation of the skeletal protein of cells, activation of inert cell precursors such as protein kinase C, and degradation of receptor proteins. It has also been shown that the abnormality of this enzyme activity is involved in many diseases, for example, refractory diseases such as cerebral apoplexy (stroke), subarachnoid hemorrhage, Alzheimer's disease, ischemic diseases, myodystrophy, cataract, platelet aggregation disorder, arthritis, and osteoporosis, among other diseases. [Trends in Pharmacological Sciences, 15, 412, 1994].

As inhibitors of such cysteine proteases, several peptide compounds inclusive of an epoxysuccinic acid peptide derivative (JP-B 1-54348, JP-A 55-153778, etc.), a peptidoaldehyde derivative (JP-B 45-17154, JP-B 46-22012, etc.), a peptidohalomethane derivative (JP-B 6-29229), and a peptidohalohydrazide derivative [Eur. J. Med. Chem., 28, 297–311, 1993] have been reported. As enzymes having calpain-inhibitory activity among various kinds of cysteine proteases, several peptide compounds such as a peptide aldehyde derivative (JP-A 6-287167), a peptidodiazomethane derivative [Biochem, J., 253, 751–758, 1988, J. Med. Chem., 35, 216–220, 1992], a peptidodisulfide derivative [Chem. Lett., 191–194, 1990], etc. and several non-peptide compounds such as an isocoumarin derivative (WO 92/11850), KP-1241 (JP-A 6-41067), etc. have also been reported. Moreover, as inhibitors of cathepsin L and B, an aldehyde derivative (JP-A 7-101924) and an epoxysuccinic acid derivative (JP-A 8-104683, WO 95/32954) have been reported.

However, many of these known inhibitors are not fully satisfactory in transferability to the cell and/or in vivo stability, while others are not as effective as desired, with the result that there is not available a clinically useful inhibitor.

DISCLOSURE OF THE INVENTION

The inventors of the present invention did much research to develop a drug substance which would show high cysteine protease-inhibitory activity and be highly membrane-permeable and comparatively stable in the in vivo environment. Consequently they discovered that a piperazine derivative of the following general formula (I) has potent cysteine protease-inhibitory activity and have perfected the present invention.

The present invention, therefore, is directed to a compound of the following formula (I) inclusive of its salt.

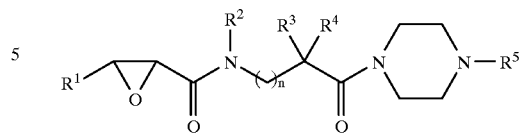

[wherein $R^1$ represents carboxy which may be esterified or amidated carboxy which may be substituted; $R^2$ represents hydrogen or lower alkyl and may be linked to either $R^3$ or $R^4$ to form a ring; $R^3$ and $R^4$ may be the same or different and each represents hydrogen, lower alkyl which may be substituted or a sulfide group which may be substituted; $R^3$ and $R^4$ may conjoinedly form a ring; $R^5$ represents a substituted phenyl group of formula (II)

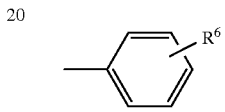

(wherein $R^6$ represents halogen or alkoxy) or a substituted sulfonyl group of formula (III)

(wherein $R^7$ represents either aryl optionally substituted by lower alkyl or amino which may be substituted); n is 0 or 1].

The present invention is further directed to a pharmaceutical composition comprising the above compound and more particularly to a cysteine protease inhibitor composition comprising said compound.

Referring to the above general formula (I), the optionally esterified carboxy represented by $R^1$ includes but is not limited to carboxy and alkoxycarboxy. The alkoxy moiety of said alkoxycarboxy may for example be $C_{1-6}$ alkoxy and preferably $C_{1-4}$ alkoxy, such as methoxy, ethoxy, propoxy, isopropoxy, butoxy, isobutoxy, sec-butoxy, and tert-butoxy. Particularly preferred is ethoxy.

The substituent for said optionally substituted amidated carboxy for $R^1$ includes hydroxy, alkoxy (methoxy, ethoxy, propoxy, etc.), and aralkyloxy (benzyloxy etc.). Preferred are hydroxy and benzyloxy.

The lower alkyl for $R^2$ includes $C_{1-6}$ straight-chain or branched-chain alkyl or preferably $C_{1-4}$ alkyl, such as methyl, ethyl, n-propyl, isopropyl, n-butyl, isobutyl, sec-butyl, tert-butyl, n-pentyl, isopentyl, neopentyl, tert-pentyl, n-hexyl, isohexyl, 4-methylpentyl, 1,1-dimethylbutyl, 2,2-dimethylbutyl, 3,3-dimethylbutyl, and 2-ethylbutyl. Preferred is hydrogen or methyl.

The ring that may be formed conjoinedly by $R^2$ and either $R^3$ or $R^4$ includes but is not limited to aziridine, azetidine, pyrrolidine, and piperidine. Particularly preferred is pyrrolidine.

The optionally substituted lower alkyl for $R^3$ and $R^4$ includes $C_{1-6}$ straight-chain or branched-chain alkyl such as methyl, ethyl, n-propyl, isopropyl, n-butyl, isobutyl, sec-butyl, tert-butyl, n-pentyl, isopentyl, neopentyl, tert-pentyl, n-hexyl, 4-methylpentyl, 1,1-dimethylbutyl, 2,2-dimethylbutyl, 3,3-dimethylbutyl, and 2-ethylbutyl. Preferred are methyl, ethyl, isobutyl, and sec-butyl. The substituent group optionally present on said alkyl includes an aromatic ring and carbamoyl. The aromatic ring mentioned just above includes aromatic carbocycles such as benzene ring and aromatic heterocycles such as indole ring. Particularly preferred is benzene ring.

The sulfide group of said optionally substituted sulfide group for $R^3$ or $R^4$ includes alkylthioalkyl groups and preferably $C_{1-4}$ alkyl-thio-$C_{1-4}$ alkyl, such as dimethyl sulfide, diethyl sulfide, dipropyl sulfide, dibutyl sulfide, dipentyl sulfide, dihexyl sulfide, methylethyl sulfide, methylpropyl sulfide, and ethylbutyl sulfide, among others. Preferred are dimethyl sulfide and methylethyl sulfide. The substituent optionally present on said sulfide group includes acylamino. The acylamino includes but is not limited to formylamino, acetylamino, propionylamino, butyrylamino, isobutyrylamino, valerylamino, isovalerylamino, pivaloylamino, and n-hexanoylamino. Preferred is acetylamino.

The ring optionally formed conjoinedly by $R^3$ and $R^4$ includes cyclopropane, cyclobutane, cyclopentane, cyclohexane and cycloheptane, etc. Particularly preferred is cyclopentane.

Referring to the substituent $R^6$ for said substituted phenyl group of formula (II), the halogen includes but is not limited to fluorine, chlorine, bromine, and iodine. Preferred are fluorine and chlorine. The halogen may be situated in any of meta, para, and ortho positions.

Referring further to the substituent $R^6$ for said substituted phenyl group of formula (II), the alkoxy includes $C_{1-6}$ alkoxy and preferably $C_{1-4}$ alkoxy, such as methoxy, ethoxy, propoxy, isopropoxy, butoxy, isobutoxy, sec-butoxy, and tert-butoxy. Particularly preferred is methoxy.

Referring to the substituent $R^7$ for the substituted sulfonyl group of formula (III), the aryl optionally substituted by lower alkyl includes but is not limited to phenyl and naphthyl. The lower alkyl optionally substituting said aryl includes methyl, ethyl, propyl, isopropyl, butyl, etc. and may be situated in any position of the aryl group.

Referring further to the substituent $R^7$ for said substituted sulfonyl group of formula (III), the amino includes amino mono- or di-substituted by $C_{1-6}$ straight-chain, branched-chain, or cyclic alkyl, such as methylamino, dimethylamino, ethylamino, diethylamino, propylamino, dipropylamino, isopropylamino, diisopropylamino, butylamino, dibutylamino, cyclohexylamino, etc. Particularly preferred is dimethylamino.

In the context of the present invention, the salt of the compound of general formula (I) is preferably a physiologically acceptable salt, thus including salts with inorganic bases, salts with organic bases, salts with inorganic acids, salts with organic acids, and salts with basic or acidic amino acids. The preferred inorganic base salt includes alkali metal salts such as sodium salt and potassium salt, alkaline earth metal salts such as calcium salt and magnesium salt, aluminum salt, and ammonium salt. The preferred organic base salt includes salts with trimethylamine, pyridine, picoline, ethanolamine, diethanolamine, triethanolamine, dicyclohexylamine, and N,N-dibenzylethylenediamine, among others. The preferred inorganic acid salt includes salts with hydrochloric acid, hydrobromic acid, nitric acid, sulfuric acid, and phosphoric acid, among others. The preferred organic acid salt includes salts with formic acid, acetic acid, trifluoroacetic acid, fumaric acid, oxalic acid, tartaric acid, maleic acid, citric acid, succinic acid, malic acid, methanesulfonic acid, benzenesulfonic acid, and p-toluenesulfonic acid, among others. The preferred salt with a basic amino acid includes salts with arginine, lysine, ornithine, etc., while the preferred salt with an acidic amino acid includes salts with aspartic acid and glutamic acid, among others.

The compound of general formula (I) according to the present invention can be produced in accordance with the following reaction scheme.

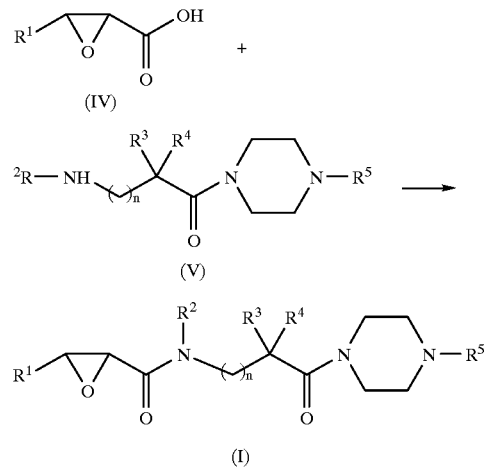

(wherein each symbol has the meaning defined hereinbefore). In this process, a compound of general formula (IV) [hereinafter sometimes referred to as compound (IV)] or a reactive derivative in the carboxyl function thereof, or a salt thereof, is reacted with a compound of general formula (V) [hereinafter sometimes referred to as compound (V)] or a reactive derivative thereof, or a salt thereof, to provide compound (I).

The above reaction can be carried out by the routine liquid-phase orsolid-phase (stationary) technique known to those skilled in peptide synthesis. As to such known routine procedures and analogous procedures, the descriptions in the following literature are incorporated herein by reference: Izumiya, Nobuo et al.: Peptide Gosei no Kiso to Jikken (Fundamentals and Experiments in Peptide Synthesis), Maruzen, 1985; Yajima, Haruaki & Sakakibara, Shumpei: Seikagaku Jikken Koza 1 (Biochemical Experiment Series 1), Japanese Biochemical Society (ed.), Tokyo Kagaku Dojin, 1977; Kimura, Toshiya: Zoku Seikagaku Jikken Koza 1 (New Biochemical Experiment Series 1, Japanese Biochemical Society (ed.), Tokyo Kgaku Dojin, 1987; Suzuki, Nobuo: Jikken Kagaku Koza (4th Edition) 22, Yuki Gosei IV (Experimental Chemistry Series (Edition IV) 22, Organic Synthesis IV), The Chemical Society of Japan (ed.), Maruzen, 1992.

The preferred reactive derivative in the carboxyl function of compound (IV) includes the acid halide, acid anhydride, activated amide, and activated ester. The acid halide includes but is not limited to the acid chloride. The acid anhydride includes mixed acid anhydrides with various acids such as substituted phosphoric acid (dialkylphosphoric acid, phenylphosphoric acid, diphenylphosphoric acid, dibenzylphosphoric acid, halophosphoric acid, etc.), dialkylphosphorous acid, sulfurous acid, thiosulfuric acid, sulfuric acid, sulfonic acids (methanesulfonic acid, etc.), aliphatic carboxylic acids (acetic acid, propionic acid, butyric acid, isobutyric acid, pivalic acid, pentanoic acid, isopentanoic acid, trichloroacetic acid, etc.), and aromatic carboxylic acids (benzoic acid etc.) as well as the symmetric acid anhydride. The preferred activated amide includes but is not limited to imidazole, 4-substituted imidazole, dimethylpyrazole, triazole, and tetrazole. The preferred activated ester includes but is not limited to the cyanomethyl ester, methoxymethyl ester, dimethyliminomethyl ester, vinyl ester, propargyl ester, p-nitrophenyl ester, trichlorophenyl ester, pentachlorophenyl ester, methylphenyl ester, phenylazophenyl ester, phenylthio ester, p-nitrophenylthio ester, p-cresylthio ester, carboxymethylthio ester, pyranyl ester, pyridyl ester, 8-quinolylthio ester, etc. and esters with N-hydroxy compounds such as N,N-dimethylhydroxylamine, 1-hydroxy-2-(1H)-pyridone, N-hydroxysuccinimide, N-hydroxyphthalimide, 1-hydroxy-1H-benzotriazole, etc. The preferred salt of compound (IV) or a reactive derivative thereof includes salts with inorganic bases such as alkali metal salts, e.g. sodium salt, potassium salt, etc., alkaline earth metal salts such as calcium salt, magnesium salt, etc., aluminum salt, and ammonium salt, as well as salts with organic bases such as trimethylamine salt, triethylamine salt, pyridine salt, picoline salt, ethanolamine salt, diethanolamine salt, triethanolamine salt, dicyclohexylamine salt, N,N-dibenzylethylenediamine salt, etc. The kind of reactive derivative can be selected according to the type of compound (IV).

The preferred reactive derivative in the amino function of compound (V) includes Schiff base type imino and enamine tautomers available on reaction of compound (V) with carbonyl compounds such as aldehydes and ketones, silyl derivatives available on reaction of compound (V) with silyl compounds such as bis(trimethylsilyl)acetamide, mono (trimethylsilyl)acetamide, bis(trimethylsilyl)urea, etc., and derivatives available on reaction of compound (V) with phosphorus trichloride or phosgene. The preferred salt of said reactive derivative of compound (V) includes salts with inorganic acids, such as hydrochloride, hydrobromide, nitrate, sulfate, phosphate, etc. and salts with organic acids, such as formate, acetate, trifluoroacetate, fumarate, oxalate, tartrate, maleate, citrate, succinate, malate, methanesulfonate, benzenesulfonate, p-toluenesulfonate, etc. These reactive derivatives can be selectively used according to the type of compound (V).

The reaction between compounds (IV) and (V) is generally conducted in the common solvent, e.g. water, alcohol (e.g. methanol, ethanol, etc.), acetone, dioxane, acetonitrile, chloroform, methylene chloride, ethylene chloride, tetrahydrofuran, ethyl acetate, N,N-dimethylformamide, and pyridine, although the reaction can be carried out in any other organic solvent that does not interfere with the reaction. The common organic solvent mentioned above may be used in admixture with water. When compound (IV) is used either in the free form or in the form of a salt in the above reaction, the reaction is preferably conducted in the presence of the common condensing agent such as N,N'-dicyclohexyl-carbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, N,N'-carbonyl-bis(2-methylimidazole), pentamethyleneketene-N-cyclohexylimine, diphenylketene-N-cyclohexylimine, ethoxyacetylene, 1-alkoxy-1-chloroethylene, trimethyl phosphite, ethyl polyphosphate, isopropyl polyphosphate, phosphorus oxychloride, diphenylphosphorylazide, thionyl chloride, oxalyl chloride, haloformic acid lower alkyl esters (e.g. ethyl chloroformate, isopropyl chloroformate, etc.), triphenylphosphine, N-hydroxybenzotriazole, 1-(p-chlorobenzenesulfonyloxy)-6-chloro-1H-benzotriazole, Vilsmeier reagents prepared by reacting N,N-dimethylformamide with thionyl chloride, phosgene, trichloromethyl chloroformate, phosphorus oxychloride, or the like. The reaction may be carried out in the presence of an inorganic or organic base, e.g. alkali metal hydrogen carbonate, tri(lower)alkylamine, pyridine, N-(lower) alkylmorpholine, N,N-di(lower)alkylbenzylamine, etc. The reaction temperature is not so critical and the reaction can be generally carried out under cooling, at ambient temperature, or under mild heating.

The structural formulas of the compounds synthesized in the examples which appear hereinafter are shown below.

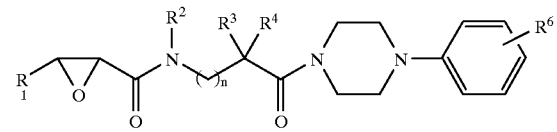

TABLE 1-1

| Ex No. | n | $R^1$ | $R^2$ | $R^3$ | $R^4$ | $R^6$ |
|---|---|---|---|---|---|---|
| 1 | 0 | —COOEt | H | benzyl | H | 4-fluoro |
| 2 | 0 | —COOEt | H | benzyl | H | 2-fluoro |
| 3 | 0 | —COOEt | H | isobutyl | H | 4-fluoro |
| 4 | 0 | —COOEt | H | isobutyl | H | H |
| 7 | 0 | —COOEt | H | isobutyl | H | 2-chloro |
| 8 | 0 | —COOEt | H | isobutyl | H | 3-chloro |
| 9 | 0 | —COOEt | H | isobutyl | H | 4-chloro |
| 10 | 0 | —COOEt | H | isobutyl | H | 4-methoxy |
| 11 | 0 | —COOEt | H | isopropyl | H | 2-chloro |
| 12 | 0 | —COOEt | H | H | H | 2-chloro |
| 13 | 0 | —COOEt | H | methyl | H | 2-chloro |
| 14 | 0 | —COOEt | H | sec-butyl | H | 2-chloro |
| 15 | 1 | —COOEt | H | H | H | 2-chloro |
| 16 | 0 | —COOEt | methyl | H | H | 2-chloro |
| 17 | 0 | —COOEt | | pyrrolidinyl | H | 2-chloro |
| 18 | 0 | —COOEt | H | —CH$_2$—S—CH$_2$NHCOCH$_3$ | H | 2-chloro |
| 19 | 0 | —COOEt | H | —CH$_2$CH$_2$—S—CH$_3$ | H | 2-chloro |
| 20 | 0 | —COOEt | H | —CH$_2$CH$_2$CONH$_2$ | H | 2-chloro |
| 21 | 0 | —COOH | H | benzyl | H | 4-chloro |
| 22 | 0 | —COOH | H | benzyl | H | 2-fluoro |
| 23 | 0 | —COOH | H | isobutyl | H | 4-fluoro |
| 24 | 0 | —COOH | H | isobutyl | H | H |

TABLE 1-1-continued

| Ex No. | n | R¹ | R² | R³ | R⁴ | R⁶ |
|---|---|---|---|---|---|---|
| 27 | 0 | —COOH | H | isobutyl | H | 2-chloro |
| 28 | 0 | —COOH | H | isobutyl | H | 3-chloro |
| 29 | 0 | —COOH | H | isobutyl | H | 4-chloro |

TABLE 1-2

| Ex. No. | n | R¹ | R² | R³ | R⁴ | R⁶ |
|---|---|---|---|---|---|---|
| 30 | 0 | —COOH | H | isobutyl | H | 4-methoxy |
| 31 | 0 | —COOH | H | isobutyl | H | 2-chloro |
| 32 | 0 | —COOH | H | H | H | 2-chloro |
| 33 | 0 | —COOH | H | methyl | H | 2-chloro |
| 34 | 0 | —COOH | H | sec-butyl | H | 2-chloro |
| 35 | 1 | —COOH | H | H | H | 2-chloro |
| 36 | 0 | —COOH | methyl | H | H | 2-chloro |
| 37 | 0 | —COOH |  | pyrrolidinyl | H | 2-chloro |
| 38 | 0 | —COOH | H | —CH₂—S—CH₂NHCOCH₃ | H | 2-chloro |
| 39 | 0 | —COOH | H | —CH₂CH₂—S—CH₃ | H | 2-chloro |
| 40 | 0 | —COOH | H | —CH₂CH₂CONH₂ | H | 2-chloro |
| 41 | 0 | —COOH | H | cyclopenyl |  | 4-fluoro |

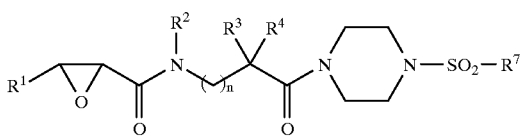

TABLE 2

| Ex. No. | n | R¹ | R² | R³ | R⁴ | R⁷ |
|---|---|---|---|---|---|---|
| 5 | 0 | —COOEt | H | isobutyl | H | —N(CH₃)₂ |
| 6 | 0 | —COOEt | H | isobutyl | H | —C₆H₄—CH₃ |
| 25 | 0 | —COOH | H | isobutyl | H | —N(CH₃)₂ |
| 26 | 0 | —COOH | H | isobutyl | H | —C₆H₄—CH₃ |
| 42 | 0 | —CONHOCH₂—C₆H₅ | H | isobutyl | H | —C₆H₄—CH₃ |
| 43 | 0 | —CONHOH | H | isobutyl | H | —C₆H₄—CH₃ |

The biological activity of the compound of the present invention is now described. The compound of general formula (I) or its salt according to the present invention has thiol protease-inhibitory activity. The inhibitory activity of the compound against calpain, cathepsin L, papain, and trypsin which is a serine protease was determined. The results are shown in Tables 3 and 4.

Assay of μ-Calpain-Inhibitory Activity

The activity of μ-calpain (Nakarai Tesque) was assayed in accordance with the procedure described in the literature [Anal. Biochem., 208, 387–392 (1993)]. Thus, to a solution containing 0.5 mg/ml casein, 50 mM Tris-HCl (pH 7.4), 20 mM dithiothreitol, and 4 mM calcium chloride was added 2.5 μl of a dimethyl sulfoxide solution containing a varying concentration of the test drug as well as 0.03 unit of μ-calpain to initiate the reaction. The final liquid volume was 250 μl. After 60 minutes of reaction at 30° C., 100 μl of the reaction mixture was transferred to another vessel, to which 50 μl of purified water and 100 μl of 50% Coumassie brilliant blue solution were added. The mixture was allowed to stand at room temperature for 15 minutes and the absorbance was measured at 595 nm. As a control, 2.5 μl of dimethyl sulfoxide not containing the test drug was added and the mixture was treated in the same manner as above. The absorbance value thus found was used as the control value. Similarly, the value found by adding 0.2 mM EDTA in lieu of 4 mM aqueous calcium chloride solution was used as the blank value. The inhibition rate was calculated by means of the following equation and plotted against concentration on log paper and the amount necessary for 50% inhibition ($IC_{50}$) was determined. E64 which is a known cysteine protease inhibition compound was used as a reference drug.

$$\text{Inhibition rate (\%)} = \left(1 - \frac{\text{Measured value} - \text{blank value}}{\text{Control value} - \text{blank value}}\right) \times 100$$

Assay of Cathepsin L-Inhibitory Activity

The activity of cathepsinL (Cosmo Bio), a cysteine protease, was assayed by the method described in the literature [Methods in Enzymology, 80, 535–561, 1981]. Thus, to a solution containing 85 mM acetate buffer (pH 5.5), 2 mM dithiothreitol, 1 mM EDTA, 2 μg cathepsin L, and a varying concentration of the test compound was added 20 μM carbobenzoxy-L-phenylalanyl-L-arginine-4-methyl-coumaryl-7-amide (Z-Phe-Arg-MCA) to initiate the reaction at the final liquid volume of 200 μl. After 20 minutes of reaction at 30° C., 20 μl of 1M Tris-HCl (pH 8.0) was added so as to stop the reaction. The amount of liberated 4-methyl-7-aminocoumarin was determined with a fluorospectrometer at an excitation wavelength of 360 nm and a fluorescent emission wavelength of 450 nm. Using the value found without addition of the test drug as control and the value found without addition of the enzyme as blank, IC50 was determined in the same manner as above. E64 was used as a reference drug.

Assay of Papain- and Trypsin-Inhibitory Activity

The activity of papain which is a cysteine protease and of trypsin (Sigma) which is a serine protease was assayed in accordance with the method described in the literature [Anal. Biochem., 208, 387–392, 1993]. Thus, to a solution containing 0.5 mg/ml casein, 50 mM Tris-HCl (pH 8.0), 20 mM dithiothreitol, and 0.2 mM EDTA was added 2.5 μl of dimethyl sulfoxide containing a varying concentration of the test drug as well as 0.03 unit of papain or trypsin to initiate the reaction. The final liquid volume was adjusted to 250 μl. After 60 minutes of reaction at 30° C., 100 μl of the reaction mixture was transferred to another vessel and following addition of 50 μl of purified water and 100 μl of 50% Coumassie brilliant blue solution, the mixture was allowed to stand at room temperature for 15 minutes. The absorbance of the mixture was then measured at 595 nm. Using the value found similarly by adding 2.5 μl of dimethyl sulfoxide not containing the test drug as control and the value found without addition of the enzyme as blank, $IC_{50}$ was determined in the same manner as above. E64 and leupeptin were used as reference drugs.

TABLE 3

| | Calpain 50% inhibitory concentration ($IC_{50}$) | | |
|---|---|---|---|
| Test drug | (μM) | Test drug | (μM) |
| E-64 | 0.66 | Example 31 | 0.95 |
| Example 3 | 47.00 | Example 32 | 17.50 |
| Example 21 | 2.90 | Example 33 | 5.10 |
| Example 23 | 0.81 | Example 34 | 0.84 |
| Example 24 | 0.78 | Example 35 | 41.00 |
| Example 25 | 1.10 | Example 37 | 2400 |
| Example 26 | 0.64 | Example 38 | 3.90 |
| Example 27 | 0.35 | Example 39 | 0.60 |
| Example 28 | 0.63 | Example 40 | 6.00 |
| Example 29 | 0.49 | Example 41 | 145 |
| Example 30 | 1.20 | Example 43 | 1.90 |

TABLE 4

| | 50% Inhibitory concentration ($IC_{50}$) | | |
|---|---|---|---|
| Test Drug | Cathepsin L (μM) | Papain (μM) | Trypsin (μM) |
| E-64 | 0.015 | 0.032 | >300 |
| Leupeptin | | | 7.4 |
| Example 21 | 0.012 | 0.110 | >3000 |
| Example 23 | 0.029 | 0.079 | >3000 |
| Example 26 | 0.082 | 0.210 | >3000 |
| Example 27 | 0.027 | 0.062 | >3000 |
| Example 32 | 37.60 | 4.00 | >3000 |
| Example 34 | 0.009 | 0.047 | >3000 |

Having inhibitory activity against cysteine proteases such as calpain, cathepsin L, and papain and showing no activity against serine protease (trypsin), the compound of general formula (I) or its salt according to the present invention is of value as a prophylactic or therapeutic agent for a variety of cysteine protease-associated diseases, for example ischemic diseases, inflammatory diseases, myodystrophy, immune diseases, essential hypertension, Alzheimer's disease, subarachnoid hemorrhage, and osteoporosis, in mammals (e.g. mouse, rat, rabbit, dog, cat, bovine, swine, and man).

The compound of general formula (I) and its salt according to the present invention can be administered systemically or locally. Systemic administration may be made not only orally but also by the intravenous, subcutaneous, intramuscular and other routes. Local administration can be made transdermally, transmucosally, intranasally or intraocularly.

The compound of general formula (I) or its salt according to the present invention can be formulated into a pharmaceutical composition. The composition that can be administered orally to man includes powders, granules, tablets, capsules, syrups, and elixirs. In the manufacture of said composition in a powdery, granular or tablet form, pharmaceutical carriers suited for solid dosage forms, such as excipients (starch, glucose, fructose, sucrose, etc.), lubricants (magnesium stearate etc.), disintegrators (starch, crystalline cellulose, etc.), binders (starch, gum arabic, etc.), etc. can be employed. Such dosage forms may be coated with a coating agent (gelatin, sucrose, etc.). For the manufacture of said composition in the form of a syrup or an elixir, such additives as stabilizers (sodium edetate etc.), suspending agents (gum arabic, calboxymethylcellulose, etc.), corrigents (simple syrup, glucose, etc.), and perfumes can be selectively employed. The composition for parenteral administration includes injections and suppositories. For the manufacture of an injection, such auxiliary agents as solvents (distilled water for injection), stabilizers (sodium edetate etc.), isotonizing agents (sodium chloride, glycerin, mannitol, etc.), pH control agents (hydrochloric acid, citric acid, sodium hydroxide, etc.), and suspending agents (methylcellulose etc.) can be employed. For the manufacture of suppositories, suppository bases (e.g. cacao butter, macrogols, etc.) and others can be selectively employed. The composition for external application includes ointments, creams, lotions, nasal drops, and eye-drops. Such compositions for external application may contain, in addition to compound (I) of the present invention, an assortment of known substances such as ointment bases (petrolatum, lanolin, etc.), solvents (saline, purified water), stabilizers (sodium edetate, citric acid, etc.), wetting agents (glycerin etc.), emulsifiers (polyvinylpyrrolidone etc.), suspending agents (hydroxypropylmethylcellulose, methylcellulose, etc.), surfactants (polysorbate 80, polyoxyethylene-hydrogenated castor oil etc.), preservatives (benzalkonium chloride, p-hydroxybenzoates, chlorobutanol, etc.), buffers (boric acid, borax, sodium acetate, citrate buffer, phosphate buffer, etc.), isotonizing agents (sodium chloride, glycerin, mannitol, etc.), pH control agent (hydrochloric acid, sodium hydroxide, etc.), and so on.

The dosage of the compound of general formula (I) or a salt thereof according to the present invention is dependent on the disease to be treated, symptoms, recipient, administration method, etc. However, the therapeutic unit oral dosage is generally 1–500 mg and preferably 10–200 mg and the therapeutic unit injection dose is generally 0.1–100 mg and preferably 1–50 mg.

EXAMPLES

The following reference, working, and formulation examples are all intended to describe the present invention in further detail and should by no means be construed as defining the scope of the invention.

Reference Example 1

To a solution of N-tert-butoxycarbonylphenyl alanine (53 g, 0.2 mol) and p-nitrophenol (27.8 g, 0.2 mol) in ethyl acetate (200 ml) on an ice-water bath was added a solution of N,N'-dicyclohexylcarbodiimide (41.2 g, 0.2 mol) in ethyl acetate (100 ml) dropwise and the mixture was stirred under cooling for 3 hours and then at room temperature for 20 hours. The precipitated byproduct N,N'-dicyclohexyl-carbodiurea was filtered off and the filtrate was concentrated under reduced pressure. The residue thus obtained was recrystallized from ethyl acetate-hexane to provide N-tert-butoxycarbonylphenylalanine p-nitrophenyl ester (61.7 g, 80%).

Reference Example 2

To a solution of N-tert-butoxycarbonylleucine (6.94 g, 30 mmol) and N-hydroxysuccinimide (3.45 g, 30 mmol) in dioxane (50 ml) on an ice-water bath was added a solution of N-ethyl-N'-(3-dimethylaminopropyl)carbodiimide hydrochloride (5.75 g, 30 mmol) in dioxane dropwise and the mixture was stirred under cooling for 20 minutes and then at room temperature for 24 hours. This reaction mixture was poured into cold water and extracted with ethyl acetate. The extract was washed with 10% aqueous citric acid solution, 10% aqueous sodium hydrogen carbonate solution, and saturated saline in the order mentioned and the organic layer was dried over anhydrous magnesium sulfate and concentrated under reduced pressure. The residue was recrystallized from isopropyl ether to provide N-tert-butoxycarbonylleucine N-hydroxysuccinimide ester (7.77 g, 78.9%).

Reference Example 3

To a solution of 1-(4-fluorophenyl)piperazine dihydrochloride (2.53 g, 10 mmol) in N,N-dimethylformamide (40 ml) were added triethylamine (2.8 ml, 20 mmol) and N-tert-butoxycarbonylphenylalanine p-nitrophenyl ester (2.65 g, 10 mmol) in the order mentioned and the mixture was stirred at room temperature overnight. This reaction mixture was poured into cold water and extracted with ethyl acetate. The extract was washed with 1% aqueous ammonia, saturated saline, 0.1N-hydrochloric acid, saturated saline, saturated aqueous sodium hydrogen carbonate solution, and saturated saline in the order mentioned and the organic layer was dried over anhydrous magnesium sulfate and further concentrated under reduced pressure. The residue was purified by silica gel column chromatography using chloroform-methanol (50:1) to provide 1,1-dimethylethyl 2-(4-(4-fluorophenyl)-1-piperazinyl)-2-oxo-1-(phenylmethyl)ethylcarbamate (2.7 g, 92.2%) as colorless oil.

Reference Example 4

Using 1- (o-fluorophenyl)piperazine monohydrochloride in lieu of 1-(4-fluorophenyl)piperazine dihydrochloride, the procedure of Reference Example 3 was otherwise repeated to provide 1,1-dimethylethyl 2-(4-(2-fluorophenyl)-1-piperazinyl)-2-oxo-1-(phenylmethyl)ethylcarbamate (1.89 g, 88.4%).

Reference Example 5

To a solution of 1-(4-fluorophenyl)piperazine dihydrochloride (0.91 g, 3 mmol) and N-tert-butoxycarbonylleucine N-hydroxysuccinimide ester (0.99 g, 3 mmol) in dichloromethane (50 ml) was added triethylamine (1.3 ml, 9 mmol) and the mixture was stirred at room temperature for 20 hours. This reaction mixture was washed with 0.1N-hydrochloric acid, saturated aqueous sodium hydrogen carbonate solution, water, and saturated saline in the order mentioned and the organic layer was dried over anhydrous magnesium sulfate and concentrated under reduced pressure. The residue was purified by silica gel column chromatography using ethyl acetate-hexane (1:1) to provide 1,1-dimethylethyl 2-(4-(4-fluorophenyl)-1-piperazinyl)-2-oxo-1-(2-methylpropyl)ethylcarbamate (1.05 g, 89.0%) as colorless oil.

Reference Example 6

Using 4-phenylpiperazine in lieu of 1-(4-fluorophenyl) piperazine dihydrochloride, the procedure of Reference Example 5 was otherwise repeated to provide 1,1-dimethylethyl 2-(4-phenyl-1-piperazinyl)-2-oxo-1-(2-methylpropyl)ethylcarbamate (7.99 g, 99%).

Reference Example 7

Using 1-dimethylsulfamoylpiperazine in lieu of 1-(4-fluorophenyl)piperazine dihydrochloride, the procedure of

Reference Example 5 was otherwise repeated to provide 1,1-dimethylethyl 2-(4-dimethylsulfamoyl-1-piperazinyl)-2-oxo-1-(2-methylpropyl)ethylcarbamate (7.19 g, 88.4%).

Reference Example 8

Using p-toluenesulfonylpiperazine in lieu of 1-(4-fluorophenyl)piperazine dihydrochloride, the procedure of Reference Example 5 was otherwise repeated to provide 1,1-dimethylethyl 2-(4-(4-methylphenylsulfonyl)-1-piperazinyl)-2-oxo-1-(2-methylpropyl)ethylcarbamate (6.95 g, 79.4%).

Reference Example 9

Using 1-(2-chlorophenyl)piperazine in lieu of 1-(4-fluorophenyl)piperazine dihydrochloride, the procedure of Reference Example 5 was otherwise repeated to provide 1,1-dimethylethyl 2-(4-(2-chlorophenyl)-1-piperazinyl)-2-oxo-1-(2-methylpropyl)ethylcarbamate (5.70 g, 95.5%).

Reference Example 10

Using 1-(m-chlorophenyl)piperazine monohydrochloride in lieu of 1-(4-fluorophenyl)piperazine dihydrochloride, the procedure of Reference Example 5 was otherwise repeated to provide 1,1-dimethylethyl 2-(4-(3-chlorophenyl)-1-piperazinyl)-2-oxo-1-(2-methylpropyl)ethylcarbamate (2.63 g, 88.4%).

Reference Example 11

Using 1-(4-chlorophenyl)piperazine monohydrochloride in lieu of 1-(4-fluorophenyl)piperazine dihydrochloride, the procedure of Reference Example 5 was otherwise repeated to provide 1,1-dimethylethyl 2-(4-(4-chlorophenyl)-1-piperazinyl)-2-oxo-1-(2-methylpropyl)ethylcarbamate (2.83 g, 94.8%).

Reference Example 12

Using N-(p-methoxyphenyl)piperazine succinate hydrochloride in lieu of 1-(4-fluorophenyl)piperazine dihydrochloride, the procedure of Reference Example 5 was otherwise repeated to provide 1,1-dimethylethyl 2-(4-(4-methoxyphenyl)-1-piperazinyl)-2-oxo-1-(2-methylpropyl)ethylcarbamate (2.73 g, 92.3%).

Reference Example 13

To a solution of 1,1-dimethylethyl 2-(4-(4-fluorophenyl)-1-piperazinyl)-2-oxo-1-(phenylmethyl)ethylcarbamate (2.7 g, 6.3 mmol) in ethyl acetate (20 mmol) on an ice bath was added 4N-HCl/ethyl acetate (20 ml) dropwise and the mixture was stirred at room temperature overnight. The resulting crystals were recovered by filtration and recrystallized from ethanol-diethyl ether to provide 1-(2-amino-1-oxo-3-phenylpropyl)-4-(4-fluorophenyl)piperazine hydrochloride (2.2g, 96.1%) as pale yellow crystals.

Reference Example 14

Using 1,1-dimethylethyl 2-(4-(2-fluorophenyl)-1-piperazinyl)-2-oxo-1-(phenylmethyl)ethylcarbamate in lieu of 1,1-dimethylethyl 2-(4-(4-fluorophenyl)-1-piperazinyl)-2-oxo-1-(phenylmethyl)ethylcarbamate, the procedure of Reference Example 13 was otherwise repeated to provide 1-(2-amino-1-oxo-3-phenylpropyl)-4-(2-fluorophenyl)piperazine hydrochloride (1.3 g, 99.1%) as white crystals.

Reference Example 15

Using 1,1-dimethylethyl 2-(4-(2-fluorophenyl)-1-piperazinyl)-2-oxo-1-(2-methylpropyl)ethylcarbamate in lieu of 1,1-dimethylethyl 2-(4-(4-fluorophenyl)-1-piperazinyl)-2-oxo-1-(phenylmethyl)ethylcarbamate, the procedure of Reference Example 13 was otherwise repeated to provide 1-(2-amino-4-methyl-1-oxopentyl)-4-(4-fluorophenyl)piperazine hydrochloride (0.56 g, 70.4%) as white crystals.

Reference Example 16

Using 1,1-dimethylethyl 2-(4-phenyl-1-piperazinyl)-2-oxo-1-(2-methylpropyl)ethylcarbamate in lieu of 1,1-dimethylethyl 2-(4-(4-fluorophenyl)-1-piperazinyl)-2-oxo-1-(phenylmethyl)ethylcarbamate, the procedure of Reference Example 13 was otherwise repeated to provide 1-(2-amino-4-methyl-1-oxopentyl)-4-phenylpiperazine hydrochloride (6.5 g, 99.2%) as white crystals.

Reference Example 17

Using 1,1-dimethylethyl 2-(4-dimethylsulfamoyl-1-piperazinyl)-2-oxo-1-(2-methylpropyl)ethylcarbamate in lieu of 1,1-dimethylethyl 2-(4-(4-fluorophenyl)-1-piperazinyl)-2-oxo-1-(phenylmethyl)ethylcarbamate, the procedure of Reference Example 13 was otherwise repeated to provide 1-(2-amino-4-methyl-1-oxopentyl)-4-dimethylsulfamoylpiperazine hydrochloride (5.0 g, 83.3%) as white crystals.

Reference Example 18

Using 1,1-dimethylethyl 2-(4-(4-methylphenylsulfonyl)-1-piperazinyl)-2-oxo-1-(2-methylpropyl) ethylcarbamate in lieu of 1,1-dimethylethyl 2-(4-(4-fluorophenyl)-1-piperazinyl)-2-oxo-1-(phenylmethyl)ethylcarbamate, the procedure of Reference Example 13 was otherwise repeated to provide 1-(2-amino-4-methyl-1-oxopentyl)-4-(4-methylphenylsulfonyl)piperazine hydrochloride (4.83 g, 78.4%) as white crystals.

Reference Example 19

Using 1,1-dimethylethyl 2-(4-(2-chlorophenyl)-1-piperazinyl)-2-oxo-1-(2-methylpropyl)ethylcarbamate in lieu of 1,1-dimethylethyl 2-(4-(4-fluorophenyl)-1-piperazinyl)-2-oxo-1-(phenylmethyl)ethylcarbamate, the procedure of Reference Example 13 was otherwise repeated to provide 1-(2-amino-4-methyl-1-oxopentyl)-4-(2-chlorophenyl)piperazine hydrochloride (1.54 g, 62.6%) as white crystals.

Reference Example 20

Using 1,1-dimethylethyl 2-(4-(3-chlorophenyl)-1-piperazinyl)-2-oxo-1-(2-methylpropyl)ethylcarbamate in lieu of 1,1-dimethylethyl 2-(4-(4-fluorophenyl)-1-piperazinyl)-2-oxo-1-(phenylmethyl)ethylcarbamate, the procedure of Reference Example 13 was otherwise repeated to provide 1-(2-amino-4-methyl-1-oxopentyl)-4-(3-chlorophenyl)piperazine hydrochloride (1.40 g, 65.7%) as white crystals.

Reference Example 21

Using 1,1-dimethylethyl 2-(4-(4-chlorophenyl)-1-piperazinyl)-2-oxo-1-(2-methylpropyl)ethylcarbamate in lieu of 1,1-dimethylethyl 2-(4-(4-fluorophenyl)-1-piperazinyl)-2-oxo-1-(phenylmethyl)ethylcarbamate, the procedure of Reference Example 13 was otherwise repeated to provide 1-(2-amino-4-methyl-1-oxopentyl)-4-(4-chlorophenyl)piperazine hydrochloride (1.50 g, 65.3%) as white crystals.

Reference Example 22

Using 1,1-dimethylethyl 2-(4-(4-methoxyphenyl)-1-piperazinyl)-2-oxo-1-(2-methylpropyl)ethylcarbamate in lieu of 1,1-dimethylethyl 2-(4-(4-fluorophenyl)-1-piperazinyl)-2-oxo-1-(phenylmethyl)ethylcarbamate, the procedure of Reference Example 13 was otherwise repeated to provide 1-(2-amino-4-methyl-1-oxopentyl)-4-(4-methoxyphenyl)piperazine hydrochloride (2.21 g, 87.4%) as white crystals.

Reference Example 23

To a solution of N-tert-butoxycarbonyl-L-valine (2.27 g, 10 mmol) and 1-(2-chlorophenyl)piperazine (2.00 g, 10 mmol) in N,N-dimethylformamide (50 ml) on an ice bath was added 1-ethyl-3-(3-dimethylaminopropyl)carbodiimide hydrochloride (2.2 g, 11 mmol) and 1-hydroxybenzotriazole (1.5 g, 11 mmol) in dichloromethane (50 ml) dropwise and the mixture was stirred at room temperature for 15 hours. The dichloromethane was then distilled off under reduced pressure and the residue was extracted with ethyl acetate (200 ml). The ethyl acetate layer was serially washed with 10% aqueous citric acid solution, saturated aqueous sodium hydrogen carbonate solution, and saturated saline in the order mentioned and dried over anhydrous sodium sulfate. The solvent was then distilled off and the residue was purified by silica gel chromatography. Elution with ethyl acetate-n-hexane (1:2, v/v) gave 1,1-dimethylethyl 2-(4-(2-chlorophenyl)piperazinyl)-2-oxo-(s)-1-(2-propyl) ethylcarbamate. After this colorless oil was dissolved in ethyl acetate (50 ml), 4N HCl/ethyl acetate (50ml) was added dropwise under ice-cooling. The mixture was stirred at room temperature for 3 hours. The reaction product was filtered and washed with ethyl acetate-n-hexane (1:1, v/v) to provide 1-((s)-2-amino-3-methyl-1-oxobutyl)-4-(2-chlorophenyl)piperazine hydrochloride (3.32 g, 95.8%) as colorless crystals.

Reference Example 24

Starting with N-tert-butoxycarbonylglycine, the procedure of Reference Example 23 was otherwise repeated to provide 1-(2-amino-1-oxoethyl)-4-(2-chlorophenyl) piperazine hydrochloride (2.4 g, 90.4%) as colorless crystals.

Reference Example 25

Starting with N-tert-butoxycarbonyl-L-alanine, the procedure of Reference Example 23 was otherwise repeated to provide 1-((s)-2-amino-1-oxopropyl)-4-(2-chlorophenyl)-piperazine hydrochloride (1.7 g, 58.8%) as colorless crystals.

Reference Example 26

Starting with N-tert-butoxycarbonyl-L-isoleucine, the procedure of Reference Example 23 was otherwise repeated to provide 1-((s)-2-amino-3-methyl-1-oxopentyl)-4-(2-chlorophenyl)piperazine hydrochloride (3.4 g, 90.2%) as colorless crystals.

Reference Example 27

Starting with N-tert-butoxycarbonyl-β-alanine, the procedure of Reference Example 23 was otherwise repeated to provide 1-(3-amino-1-oxopropyl)-4-(2-chlorophenyl) piperazine hydrochloride (2.9 g, 90.0%) as colorless crystals.

Reference Example 28

Starting with N-tert-butoxycarbonylsarcosine, the procedure of Reference Example 23 was otherwise repeated to provide 1-(2-methylamino-1-oxoethyl)-4-( 2-chlorophenyl) piperazine hydrochloride (3.0 g, 93.3%) as colorless crystals.

Reference Example 29

Starting with N-tert-butoxycarbonyl-L-proline, the procedure of Reference Example 23 was otherwise repeated to provide 1-(1-(2-pyrrolidinyl)-1-oxomethyl)-4-(2-chlorophenyl)piperazine hydrochloride (4.3 g, 98.0%) as colorless crystals.

Reference Example 30

Starting with N-tert-butoxycarbonyl-(s-acetamidomethyl)-L-cysteine, the procedure of Reference Example 23 was otherwise repeated to provide 1-((s)-2-amino-3-(acetylaminomethylthio)-1-oxopropyl)-4-(2-chlorophenyl)piperazine hydrochloride (4.0 g, 95.9%) as colorless crystals.

Reference Example 31

Starting with N-tert-butoxycarbonyl-L-methionine, the procedure of Reference Example 23 was otherwise repeated to provide 1-((s)-2-amino-4-methylthio-1-oxobutyl)-4-(2-chlorophenyl)piperazine hydrochloride (3.7 g, 97.1%) as colorless crystals.

Reference Example 32

Starting with N-tert-butoxycarbonyl-L-glutamine, the procedure of Reference Example 23 was otherwise repeated to provide 1-((s)-2-amino-4-carbamoyl-1-oxobutyl)-4-(2-chlorophenyl)piperazine hydrochloride (2.7 g, 60.7%) as colorless crystals.

Example 1

To a solution of 1-(2-amino-1-oxo-3-phenylpropyl)-4-(4-fluorophenyl)piperazine hydrochloride (1.82 g, 5 mmol) in N,N-dimethylformamide (20 ml) was added triethylamine (0.697 ml, 5 mmol) and the mixture was stirred at room temperature for 10 minutes. To this reaction mixture was added ethyl p-nitrophenyl L-trans-epoxysuccinate, synthesized in accordance with the method of Tamai et al. [Chem. Pharm. Bull., 35, 1098 (1987)] (1.41 g, 5 mmol), and the mixture was stirred at room temperature for 20 hours. This reaction mixture was poured into cold water and extracted with ethyl acetate. The extract was serially washed with 1% aqueous ammonia, saturated saline, 0.1N-hydrochloric acid, saturated saline, saturated aqueous sodium hydrogen carbonate solution, and saturated saline in the order mentioned and the organic layer was dried over anhydrous magnesium sulfate and concentrated under reduced pressure. The residue was subjected to silica gel chromatography, elution being carried out with ethyl acetate-hexane (1:1). The procedure provided ethyl (2s,3s)-3-[[[[(1s)-1-[[4-(4-fluorophenyl)-1-piperadinyl]carbo nyl]-2-phenyl]ethyl] amino]carbonyl]oxiranecarboxylate (1.2 g, 51.1%).

$^1$H NMR (CDCl$_3$) δ: 1.31 (t, 3H, J=7.0 Hz), —C—CH$_3$), 2.42–2.50 (m, 1H, piperazine ring), 2.83–2.94 (m, 2H, piperazine ring), 3.00 (d, 2H, J=7.6 Hz, ph—CH$_2$—C—), 2.97–3.07 (m, 1H, piperazine ring), 3.14–3.22 (m, 1H, piperazine ring), 3.35 (d, 1H, J=1.9 Hz, epoxy ring), 3.43–3.52 (m, 1H, piperazine ring), 3.64 (d, 1H, J=1.9 Hz, epoxy ring), 3.71 (t, 2H, J=5.4 Hz, piperazine ring), 4.25 (dq, 2H, J=7.3, 2.6 Hz, —O—CH$_2$—C), 5.18 (q, 1H, J=5.3 Hz, —N—CH—CO), 6.75–6.83 (m, 2H, aromatic), 6.91–7.04 (m, 2H, aromatic, 1H, NH), 7.17–7.34 (m, 5H, aromatic).

Example 2

Using 1-(2-amino-1-oxo-3-phenylpropyl)-4-(2-fluorophenyl)piperazine hydrochloride in lieu of 1-(2-amino-1-oxo-3-phenylpropyl)-4-(4-fluorophenyl)piperazine hydrochloride, the procedure of Example 1 was otherwise repeated to provide ethyl (2s, 3s)-3-[[[[(1s)-1-[[4-(2-fluorophenyl)-1-piperazinyl]carbonyl]-2-phenyl]ethyl]amino]carbonyl]oxiranecarboxylate (0.83 g, 58.6%).

$^1$H NMR (CDCl$_3$) δ: 1.31 (t, 3H, J=7.1 Hz, —C—CH$_3$), 2.42–2.49 (m, 1H, piperazine ring), 2.72–2.90 (m, 2H, piperazine ring), 3.02 (d, 2H, J=8.3 Hz, ph—CH$_2$—C—), 2.94–3.10 (m, 1H, piperazine ring), 3.17–3.29 (m, 1H, piperazine ring), 3.36 (d, 1H, J=1.7 Hz, epoxy ring), 3.44–3.57 (m, 1H, piperazine ring), 3.65 (d, 1H, J=1.3 Hz, epoxy ring), 3.66–3.80 (m, 2H, piperazine ring), 4.25 (dq, 2H, J=7.1, 2.3 Hz, —O—CH$_2$—C), 5.19 (q, 1H, J=7.6 Hz, —N—CH—CO), 6.8 (t, 1H, J=8.3 Hz, —NH—), 6.93–7.11 (m, 4H, aromatic), 7.18–7.34 (m, 5H, aromatic).

Example 3

Using 1-(2-amino-4-methyl-1-oxopentyl)-4-(4-fluorophenyl)piperazine hydrochloride in lieu of 1-(2-amino-1-oxo-3-phenylpropyl)-4-(4-fluorophenyl)piperazine hydrochloride, the procedure of Example 1 was otherwise repeated to provide ethyl (2s,3s)-3-[[[[(1s)-1-[[4-(4-fluorophenyl)-1-piperazinyl]carbonyl]-3-methyl]butyl]amino]carbonyl]oxiranecarboxylate (0.30 g, 45.6%).

$^1$H NMR (CDCl$_3$) δ: 0.93 (d, 3H, J=6.3 Hz, —C—CH$_3$), 1.00 (d, 3H, J=6.3 Hz, —C—CH$_3$), 1.32 (t, 3H, J=7.3 Hz, —C—CH$_3$), 1.40–1.63 (m, 3H, —C—CH$_2$—CH—C$_2$), 3.06–3.15 (m, 4H, piperazine ring), 3.49 (d, 1H, J=1.7 Hz, epoxy ring), 3.60–3.89 (m, 4H, piperazine ring), 3.68 (d, 1H, J=1.7 Hz, epoxy ring), 4.26 (dq, 2H, J=7.3, 3.3 Hz, —O—CH$_2$—C), 5.03 (dt, 1H, J=8.91, 4.3 Hz, —N—CH—CO), 6.85–7.03 (m, 5H, aromatic and —NH).

Example 4

Using 1-(2-amino-4-methyl-1-oxopentyl)-4-phenylpiperazine hydrochloride in lieu of 1-(2-amino-1-oxo-3-phenylpropyl)-4-(4-fluorophenyl)piperazine hydrochloride, the procedure of Example 1 was otherwise repeated to provide ethyl (2s,3s)-3-[[[[(1s)-1-[(4-phenyl-1-piperazinyl)carbonyl]-3-methyl]butyl]amino]carbonyl]oxiranecarboxylate (3.96 g, 63.3%).

$^1$H NMR (CDCl$_3$) δ: 0.93 (d, 3H, J=6.3 Hz, —C—CH$_3$), 1.00 (d, 3H, J=6.3 Hz, —C—CH$_3$), 1.32 (t, 3H, J=7.3 Hz, —C—CH$_3$), 1.40–1.63 (m, 3H, —C—CH$_2$—CH—C$_2$), 3.16–3.24 (m, 4H, piperazine ring), 3.49 (d, 1H, J=1.7 Hz, epoxy ring), 3.60–3.89 (m, 4H, piperazine ring), 3.68 (d, 1H, J=1.7 Hz, epoxy ring), 4.26 (dq, 2H, J=7.3, 3.3 Hz, —O—CH$_2$—C), 5.03 (dt, 1H, J=8.9, 4.3 Hz, —N—CH—CO), 6.90–6.95 (m, 4H, aromatic and —NH), 7.25–7.33 (m, 2H, aromatic).

Example 5

Using 1-(2-amino-4-methyl-1-oxopentyl)-4-dimethylsulfamoylpiperazine hydrochloride in lieu of 1-(2-amino-1-oxo-3-phenylpropyl)-4-(4-fluorophenyl)piperazine hydrochloride, the procedure of Example 1 was otherwise repeated to provide ethyl (2s,3s)-3-[[[[(1s)-1-[(4-dimethylsulfamoyl-1-piperazinyl)carbonyl]-3-methyl]butyl]amino]carbonyl]oxirane carboxylate (3.7 g, 82.6%).

$^1$H NMR (CDCl$_3$) δ: 0.92 (d, 3H, J=6.3 Hz, —C—CH$_3$), 0.89 (d, 3H, J=6.3 Hz, —C—CH$_3$), 1.32 (t, 3H, J=7.3 Hz, —C—CH$_3$), 1.38–1.60 (m, 3H, —C—CH$_2$—CH—C$_2$), 2.85 (s, 6H, —N—CH$_3$), 3.15–3.38 (m, 4H, piperazine ring), 3.48 (d, 1H, J=1.7 Hz, epoxy ring), 3.52–3.68 (m, 3H, piperazine ring), 3.67 (d, 1H, J=1.7 Hz, epoxy ring), 3.79–3.87 (m, 1H, piperazine ring), 4.27 (dq, 2H, J=7.3, 4.0 Hz, —O—CH$_2$—C), 4.96 (dt, 1H, J=8.9, 4.3 Hz, —N—CH—CO), 6.90 (d, 1H, J=8.6 Hz, —NH—).

Example 6

Using 1-(2-amino-4-methyl-1-oxopentyl)-4-(4-methylphenylsulfonyl)piperazine hydrochloride in lieu of 1-(2-amino-1-oxo-3-phenylpropyl)-4-(4-fluorophenyl)piperazine hydrochloride, the procedure of Example 1 was otherwise repeated to provide ethyl (2s,3s)-3-[[[[(2s)-1-[[4-(4-methylphenyl-sulfonyl)-1-piperazinyl]carbonyl]-3-methyl]butyl]-amino]carbonyl]oxiranecarboxylate (4.31 g, 95.1%).

$^1$H NMR (CDCl$_3$) δ: 0.87 (d, 3H, J=6.3 Hz, —C—CH$_3$), 0.94 (d, 3H, J=6.3 Hz, —C—CH$_3$), 1.30 (t, 3H, J=7.3 Hz, —C—CH$_3$), 1.31–1.55 (m, 3H, —C—CH$_2$—CH—C$_2$), 2.45 (s, 6H, —ph—CH$_3$), 2.70–2.84 (m, 2H, piperazine ring), 3.22–3.54 (m, 4H, piperazine ring), 3.43 (d, 1H, J=1.7 Hz, epoxy ring), 3.61 (d, 1H, J=2.0 Hz, epoxy ring), 3.68–3.78 (m, 1H, piperazine ring), 3.96–4.06 (m, 1H, piperazine ring), 4.25 (dq, 2H, J=7.3, 4.0 Hz, —O—CH$_2$—C), 4.87 (dt, 1H, J=9.2, 4.0 Hz, —N—CH—CO), 6.81 (d, 1H, J=8.6 Hz, —NH—), 7.35 (d, 2H, J=7.9 Hz, aromatic), 7.63 (d, 2H, J=8.3 Hz, aromatic)

Example 7

Using 1-(2-amino-4-methyl-1-oxopentyl)-4-(2-chlorophenyl)piperazine hydrochloride in lieu of 1-(2-amino-1-oxo-3-phenylpropyl)-4-(4-fluorophenyl)piperazine hydrochloride, the procedure of Example 1 was otherwise repeated to provide ethyl (2s,3s)-3-[[[[(1)-1-[[4-(2-chlorophenyl)-1-piperazinyl]carbonyl]-3-methyl]butyl]amino]carbonyl]oxiranecarboxylate (0.65 g, 35.9%).

$^1$H NMR (CDCl$_3$) δ: 0.93 (d, 3H, J=6.3 Hz, —C—CH$_3$), 1.01 (d, 3H, J=6.3 Hz, —C—CH$_3$), 1.32 (t, 3H, J=7.3 Hz, —C—CH$_3$), 1.41–1.61 (m, 3H, —C—CH$_2$—CH—C$_2$), 2.96–3.10 (m, 4H, piperazine ring), 3.49 (d, 1H, J=2.0 Hz, epoxy ring), 3.61–3.81 (m, 3H, piperazine ring), 3.68 (d, 1H, J=2.0 Hz, epoxy ring), 3.90–3.98 (m, 1H, piperazine ring), 4.27 (dq, 2H, J=7.3, 4.0 Hz, —O—CH$_2$—C), 5.03 (dt, 1H, J=8.9, 4.3 Hz, —N—CH—CO), 6.91 (d, 1H, J=8.6 Hz, —NH—), 7.00–7.06 (m, 2H, aromatic), 7.21–7.27 (m, 1H, aromatic), 7.37–7.41 (m, 1H, aromatic).

Example 8

Using 1-(2-amino-4-methyl-1-oxopentyl)-4-(3-chlorophenyl)piperazine hydrochloride in lieu of 1-(2-amino-1-oxo-3-phenylpropyl)-4-(4-fluorophenyl)piperazine hydrochloride, the procedure of Example 1 was otherwise repeated to provide ethyl (2s,3s)-3-[[[[(1)-1-[[4-(3-chlorophenyl)-1-piperazinyl]carbonyl]-3-methyl]butyl]amino]carbonyl]oxiranecarboxylate (1.24 g, 68.4%).

$^1$H NMR (CDCl$_3$) δ: 0.93 (d, 3H, J=6.3 Hz, —C—CH$_3$), 1.00 (d, 3H, J=6.3 Hz, —C—CH$_3$), 1.32 (t, 3H, J=7.3 Hz, —C—CH$_3$), 1.42–1.63 (m, 3H, —C—CH$_2$—CH—C$_2$), 3.17–3.25 (m, 4H, piperazine ring), 3.48 (d, 1H, J=2.0 Hz, epoxy ring), 3.60–3.90 (m, 4H, piperazine ring), 3.67 (d, 1H, J=2.0 Hz, epoxy ring), 4.27 (dq, 2H, J=7.3, 4.0 Hz, —O—CH$_2$—C), 5.02 (dt, 1H, J=8.9, 4.3 Hz, —N—CH—CO), 6.77–6.81 (m, 1H, aromatic), 6.86–6.89 (m, 3H, aromatic and —NH), 7.16–7.22 (m, 1H, aromatic).

Example 9

Using 1-(2-amino-4-methyl-1-oxopentyl)-4-(4-chlorophenyl)piperazine hydrochloride in lieu of 1-(2-amino-1-oxo-3-phenylpropyl)-4-(4-fluorophenyl)piperazine hydrochloride, the procedure of Example 1 was otherwise repeated to provide ethyl (2s,3s)-3-[[[[(1)-1-[[4-(4-chlorophenyl)-1-piperazinyl]carbonyl]-3-methyl]butyl]amino]carbonyl]oxiranecarboxylate (0.55 g, 27.1%).

$^1$H NMR (CDCl$_3$) δ: 0.93 (d, 3H, J=6.3 Hz, —C—CH$_3$), 1.0 (d, 3H, J=6.3 Hz, —C—CH$_3$), 1.32 (t, 3H, J=7.3 Hz, —C—CH$_3$), 1.42–1.63 (m, 3H, —C—CH$_2$—CH—C$_2$), 3.12–3.20 (m, 4H, piperazine ring), 3.48 (d, 1H, J=2.0 Hz, epoxy ring), 3.60–3.90 (m, 4H, piperazine ring), 3.67 (d, 1H, J=2.0 Hz, epoxy ring), 4.27 (dq, 2H, J=7.3, 4.0 Hz, —O—CH$_2$—C), 5.02 (dt, 1H, J=8.9, 4.3 Hz, —N—CH—CO), 6.83–6.87 (m, 2H, aromatic), 6.90 (d, 1H, J=9.9 Hz, —NH), 7.21–7.3 (m, 2H, aromatic).

Example 10

Using 1-(2-amino-4-methyl-1-oxopentyl)-4-(4-methoxyphenyl)piperazine hydrochloride in lieu of 1-(2-amino-1-oxo-3-phenylpropyl)-4-(4-fluorophenyl)piperazine hydrochloride, the procedure of Example 1 was otherwise repeated to provide ethyl (2s,3s)-3-[[[[(1)-1-[[4-(4-methoxyphenyl)-1-piperazinyl]carbonyl]-3-methyl]butyl]amino]carbonyl]oxiranecarboxylate (0.94 g, 65.2%).

$^1$H NMR (CDCl$_3$) δ: 0.92 (d, 3H, J=6.6 Hz, —C—CH$_3$), 1.00 (d, 3H, J=6.3 Hz, —C—CH$_3$), 1.32 (t, 3H, J=7.3 Hz, —C—CH$_3$), 1.40–1.60 (m, 3H, —C—CH$_2$—CH—C$_2$), 3.03–3.11 (m, 4H, piperazine ring), 3.49 (d, 1H, J=2.0 Hz, epoxy ring), 3.60–3.88 (m, 4H, piperazine ring), 3.67 (d, 1H, J=2.0 Hz, epoxy ring), 3.78 (s, 3H, —O—CH$_3$), 4.27 (dq, 2H, J=7.3, 4.0 Hz, —O—CH$_2$—C), 5.03 (dt, 1H, J=8.9, 4.3 Hz, —N—CH—CO), 6.83–6.96 (m, 5H, aromatic and —NH).

Example 11

Using 1-((s)-2-amino-3-methyl-1-oxobutyl)-4-(2-chlorophenyl)piperazine hydrochloride in lieu of 1-(2-amino-1-oxo-3-phenylpropyl)-4-(4-fluorophenyl)piperazine hydrochloride, the procedure of Example 1 was otherwise repeated to provide ethyl (2s,3s)-3-[[[[(1)-1-[[4-(2-chlorophenyl)-1-piperazinyl]carbonyl]-2-methyl]propyl]amino]carbonyl]oxiranecarboxylate (1.3 g, 57.4%) as colorless oil.

Example 12

Using 1-(2-amino-1-oxoethyl)-4-(2-chlorophenyl)piperazine hydrochloride in lieu of 1-(2-amino-1-oxo-3-phenylpropyl)-4-(4-fluorophenyl)piperazine hydrochloride, the procedure of Example 1 was otherwise repeated to provide ethyl (2s,3s)-3-[[[[4-(2-chlorophenyl)-1-piperazinyl]carbonyl]methyl]amino]carbonyl]oxiranecarboxylate (1.75 g, 53.5%) as colorless oil.

Example 13

Using 1-((s)-2-amino-1-oxopropyl)-4-(2-chlorophenyl)-piperazine hydrochloride in lieu of 1-(2-amino-1-oxo-3-phenylpropyl)-4-(4-fluorophenyl)piperazine hydrochloride, the procedure of Example 1 was otherwise repeated to provide ethyl (2s,3s)-3-[[[(1)-1-[[4-(2-chlorophenyl)-1-piperazinyl]carbonyl]ethyl]amino]carbonyl]oxiranecarboxylate (1.23 g, 55.0%) as colorless oil.

Example 14

Using 1-((s)-2-amino-3-methyl-1-oxopentyl)-4-(2-chlorophenyl)piperazine hydrochloride in lieu of 1-(2-amino-1-oxo-3-phenylpropyl)-4-(4-fluorophenyl)piperazine hydrochloride, the procedure of Example 1 was otherwise repeated to provide ethyl (2s,3s)-3-[[[[(1)-1-[[4-(2-chlorophenyl)-1-piperazinyl]carbonyl]-2-methyl]butyl]amino]carbonyl]oxiranecarboxylate (1.48 g, 56.6%) as colorless oil.

Example 15

Using 1-(3-amino-1-oxopropyl)-4-(2-chlorophenyl)piperazine hydrochloride in lieu of 1-(2-amino-1-oxo-3-phenylpropyl)-4-(4-fluorophenyl)piperazine hydrochloride, the procedure of Example 1 was otherwise repeated to provide ethyl (2s,3s)-3-[[[2-[[4-(2-chlorophenyl)-1-piperazinyl]carbonyl]ethyl]amino]carbonyl]oxiranecarboxylate (1.16 g, 52.9%) as colorless oil.

Example 16

Using 1-(2-methylamino-1-oxoethyl)-4-(2-chlorophenyl)piperazine hydrochloride in lieu of 1-(2-amino-1-oxo-3-phenylpropyl)-4-(4-fluorophenyl)piperazine hydrochloride, the procedure of Example 1 was otherwise repeated to provide ethyl (2s,3s)-3-[[[[N-[[4-(2-chlorophenyl)-1-piperazinyl]carbonyl]methyl]-N-methyl]amino]carbonyl]oxiranecarboxylate (1.55 g, 76.7%) as colorless oil.

Example 17

Using 1-(1-(2-pyrrolidinyl)-1-oxomethyl)-4-(2-chlorophenyl)piperazine hydrochloride in lieu of 1-(2-amino-1-oxo-3-phenylpropyl)-4-(4-fluorophenyl)piperazine hydrochloride, the procedure of Example 1 was otherwise repeated to provide ethyl (2s,3s)-3-[[(2s)-2-[[4-(2-chlorophenyl)-1-piperazinyl]carbonyl]-1-pyrrolidinyl]carbonyl]oxiranecarboxylate (1.42 g, 49.9%) as colorless oil.

Example 18

Using 1-((s)-2-amino-3-(acetylaminomethylthio)-1-oxopropyl)-4-(2-chlorophenyl)piperazine hydrochloride in lieu of 1-(2-amino-1-oxo-3-phenylpropyl)-4-(4-fluorophenyl)piperazine hydrochloride, the procedure of Example 1 was otherwise repeated to provide ethyl (2s,3s)-3-[[[[(1)-1-[[4-(2-chlorophenyl)-1-piperazinyl]carbonyl]-2-acetylaminomethylthio]ethyl]amino]carbonyl]oxiranecarboxylate (1.19 g, 43.7%) as colorless oil.

Example 19

Using 1-((s)-2-amino-4-methylthio-1-oxobutyl)-4-(2-chlorophenyl)piperazine hydrochloride in lieu of 1-(2-amino-1-oxo-3-phenylpropyl)-4-(4-fluorophenyl)piperazine hydrochloride, the procedure of Example 1 was otherwise repeated to provide ethyl (2s,3s)-3-[[[[(1)-1-[[4-(2-chlorophenyl)-1-piperazinyl]carbonyl]-4-methylthio]butyl]amino]carbonyl]oxiranecarboxylate (1.54 g, 61.5%) as colorless oil.

Example 20

Using 1-((s)-2-amino-4-carbamoyl-1-oxobutyl)-4-(2-chlorophenyl)piperazine hydrochloride in lieu of 1-(2- amino-1-oxo-3-phenylpropyl)-4-(4-fluorophenyl)piperazine hydrochloride, the procedure of Example 1 was otherwise repeated to provide ethyl (2s,3s)-3-[[[[(1)-1-[[4-(2-chlorophenyl)-1-piperazinyl]carbonyl]-3-carbamoyl] propyl]amino]carbonyl]oxiranecarboxylate (0.2 g, 5.8%) as colorless oil.

Example 21

To a solution of ethyl (2s,3s)-3-[[[[(1)-1-[[4-(4-fluorophenyl)-1-piperazinyl]carbonyl]-2-phenyl]ethyl] amino]carbonyl]oxiranecarboxylate (0.5 g, 1.06 mmol) in ethanol (20 ml) on an ice-water bath was added 0.1N-sodium hydroxide/ethanol (16 ml) and the mixture was stirred at room temperature for 20 hours. This reaction mixture was poured into cold water and acidified with 1N-hydrochloric acid and the resulting white precipitate was recovered by filtration and dried. This precipitate was recrystallized from ethyl acetate-hexane to provide (2s,3s)-3-[[[[(1s)-1-[[4-(4-fluorophenyl)-1-piperazinyl]carbonyl]-2-phenyl]ethyl]amino]carbonyl]oxiranecarboxylic acid (0.36 g, 77.8%).

$^1$H NMR (CDCl$_3$) δ: 2.34–2.41 (m, 1H, piperazine ring), 2.82–2.96 (m, 2H, piperazine ring), 2.99–3.08 (m, 1H, piperazine ring), 3.06 (d, 2H, J=7.3 Hz, ph—CH$_2$—C—), 3.16–3.24 (m, 1H, piperazine ring), 3.49–3.58 (m, 1H, piperazine ring), 3.55 (d, 1H, J=1.7 Hz, epoxy ring), 3.57 (d, 1H, J=1.7 Hz, epoxy ring), 3.71 (t, 2H, J=5.1 Hz, piperazine ring), 4.5–6.0 (br d, 1H, —COOH), 5.23 (q, 1H, J=7.9 Hz, —N—CH—CO), 6.74–6.82 (m, 2H, aromatic), 6.91–7.00 (m, 2H, aromatic), 7.20–7.35 (m, 5H, aromatic), 8.23 (d, 1H, J=8.6 Hz, —NH—).

Example 22

Using ethyl (2s,3s)-3-[[[[(1s)-1-[[4-(2-fluorophenyl)1-piperazinyl]carbonyl]-2-phenyl]ethyl]amino]carbonyl] oxiranecarboxylate in lieu of ethyl (2s,3s)-3-[[[[(1s)-1-[[4-(4-fluorophenyl)-1-piperazinyl]carbonyl]-2-phenyl]ethyl] amino]carbonyl]oxiranecarboxylate, the procedure of Example 21 was otherwise repeated to provide ((2s,3s)-3-[[[[(1s)-1-[[4-(2-fluorophenyl)-1-piperazinyl]carbonyl]-2-phenyl]ethyl]amino]carbonyl]oxiranecarboxylic acid (0.1 g, 29.6%).

$^1$H NMR (CDCl$_3$) δ: 2.38–2.43 (m, 1H, piperazine ring), 2.83–2.93 (m, 2H, piperazine ring), 2.95–3.08 (m, 1H, piperazine ring), 3.06 (d, 2H, J=7.6 Hz, ph—CH$_2$—C—), 3.20–3.28 (m, 1H, piperazine ring), 3.49–3.66 (m, 1H, piperazine ring), 3.55 (d, 1H, J=1.7 Hz, epoxy ring), 3.58 (d, 1H, J=1.3 Hz, epoxy ring), 3.67–3.80 (m, 2H, piperazine ring), 4.0–6.0 (br d, 1H, —COOH), 5.23 (q, 1H, J=7.9 Hz, —N—CH—CO), 6.77–6.87 (m, 1H, aromatic), 6.93–7.09 (m, 3H, aromatic), 7.20–7.36 (m, 5H, aromatic), 8.23 (d, 1H, J=8.6 Hz, —NH—).

Example 23

Using ethyl (2s,3s)-3-[[[[(1)-1-[[4-(4-fluorophenyl)-1-piperazinyl]carbonyl]-3-methyl]butyl]amino]carbonyl] oxiranecarboxylate in lieu of ethyl (2s,3s)-3-[[[[(1s)-1-[[4-(4-fluorophenyl)-1-piperazinyl]carbonyl]-2-phenyl]ethyl] amino]carbonyl]oxiranecarboxylate, the procedure of Example 21 was otherwise repeated to provide (2s,3s)-3-[[[[(1s)-1-[[4-(4-fluorophenyl)-1-piperazinyl]carbonyl]-3-methyl]butyl]amino]carbonyl]oxiranecarboxylic acid (0.13 g, 69.5%).

$^1$H NMR (CDCl$_3$) δ: 0.96 (d, 3H, J=6.6 Hz, —C—CH$_3$), 0.99 (d, 3H, J=6.59 Hz, —C—CH$_3$), 1.42 (ddd, 1H, J=14.1, 10.5, 3.6 Hz, —C—CH$_2$—C), 1.6–1.82 (m, 1H, —C—CH—C$_2$), 1.69 (ddd, 1H, J=14.5, 10.7, 4.23 Hz, —C—CH$_2$—C), 3.08–3.26 (m, 4H, piperazine ring), 3.55 (d, 1H, J=1.7 Hz, epoxy ring), 3.60–3.92 (m, 4H, piperazine ring), 3.62 (d, 1H, J=1.8 Hz, epoxy ring), 5.08 (ddd, 1H, J=10.6, 8.6, 3.6 Hz, —N—CH—CO), 5.2–6.4 (br d, 1H, —COOH), 6.84–7.03 (m, 4H, aromatic), 8.18 (d, 1H, J=8.6 Hz, —NH—).

Example 24

Using ethyl (2s,3s)-3-[[[[(1s)-1-[(4-phenyl-1-piperazinyl) carbonyl]-3-methyl]butyl]amino]carbonyl] oxiranecarboxylate in lieu of ethyl (2s,3s)-3-[[[[(1s)-1-[[4-(4-fluorophenyl)-1-piperazinyl]carbonyl]-2-phenyl]-ethyl] amino]carbonyl]oxiranecarboxylate, the procedure of Example 21 was otherwise repeated to provide (2s,3s)-3-[[[[(1s)-1-[(4-phenyl-1-piperazinyl)carbonyl]-3-methyl] butyl]amino]carbonyl]oxiranecarboxylic acid (1.06 g, 29.1%).

$^1$H NMR (CDCl$_3$) δ: 0.96 (d, 3H, J=6.6 Hz, —C—CH$_3$), 0.99 (d, 3H, J=6.26 Hz, —C—CH$_3$), 1.37–1.47 (m, 1H, —C—CH—C$_2$), 1.64–1.80 (m, 2H, —C—CH$_2$—C—), 3.17–3.36 (m, 4H, piperazine ring), 3.55 (d, 1H, J=1.7 Hz, epoxy ring), 3.62 (d, 1H, J=1.3 Hz, epoxy ring), 3.70–3.90 (m, 4H, piperazine ring), 5.10 (m, 1H, —N—CH—CO), 6.5–7.5 (br d, 1H, —COOH), 6.87–6.96 (m, 3H, aromatic), 7.27–7.33 (m, 2H, aromatic), 8.20 (d, 1H, J=8.6 Hz, —NH—).

Example 25

Using ethyl (2s,3s)-3-[[[[(1s)-1-[(4-dimethylsulfamoyl-1-piperazinyl)carbonyl]-3-methyl]butyl]amino]carbonyl] oxiranecarboxylate in lieu of ethyl (2s,3s)-3-[[[[(1s)-1-[[4-(4-fluorophenyl)-1-piperazinyl]carbonyl]-2-phenyl]ethyl] amino]carbonyl]oxiranecarboxylate, the procedure of Example 21 was otherwise repeated to provide (2s,3s)-3-[[[[(1s)-1-[(4-dimethylsulfamoyl-1-piperazinyl)carbonyl]-3-methyl]butyl]amino]carbonyl]oxiranecarboxylic acid (1.28 g, 39.0%).

$^1$H NMR (CDCl$_3$) δ: 0.94 (d, 3H, J=6.3 Hz, —C—CH$_3$), 0.96 (d, 3H, J=5.6 Hz, —C—CH$_3$), 1.36–1.44 (m, 1H, —C—CH—C$_2$), 1.61–1.68 (m, 2H, —C—CH$_2$—C—), 2.85 (s, 6H, —N—CH$_3$), 3.17–3.35 (m, 4H, piperazine ring), 3.48–3.60 (m, 2H, piperazine ring), 3.58 (d, 1H, J=1.7 Hz, epoxy ring), 3.62 (d, 1H, J=1.7 Hz, epoxy ring), 3.70–3.80 (m, 1H, piperazine ring), 3.83–3.95 (m, 1H, piperazine ring), 4.95–5.05 (m, 1H, —N—CH—CO), 7.7–8.1 (br d, 1H, —COOH), 7.94 (d, 1H, J=8.6 Hz, —NH—).

Example 26

Using ethyl (2s,3s)-3-[[[[(1s)-1-[[4-(4-methylphenylsulfonyl)-1-piperazinyl]carbonyl]-3-methyl] butyl]amino]carbonyl]oxiranecarboxylate in lieu of ethyl (2s,3s)-1-[[[[(1s)[[4-(4-fluorophenyl)-1-piperazinyl] carbonyl]-2-phenyl]ethyl]amino]carbonyl] oxiranecarboxylate, the procedure of Example 21 was otherwise repeated to provide (2s,3s)-3-[[[[(1s)-1-[[4-(4-methylphenylsulfonyl)-1-piperazinyl]carbonyl]-3-methyl] butyl]amino]carbonyl]oxiranecarboxylic acid (2.8 g, 70.0%).

$^1$H NMR (CDCl$_3$) δ: 0.90 (d, 3H, J=6.6 Hz, —C—CH$_3$), 0.93 (d, 3H, J=6.6 Hz, —C—CH$_3$), 1.23–1.33 (m, 1H, —C—CH—C$_2$), 1.53–1.67 (m, 2H, —C—CH$_2$—C—), 2.45 (s, 3H, —ph—CH$_3$), 2.73–2.91 (m, 2H, piperazine ring), 3.28–3.59 (m, 4H, piperazine ring), 3.45 (d, 1H, J=1.7 Hz, epoxy ring), 3.48 (d, 1H, J=1.7 Hz, epoxy ring), 3.70–3.83 (m, 1H, piperazine ring), 3.98–4.08 (m, 1H, piperazine ring), 4.85–4.97 (m, 1H, —N—CH—CO), 7.35 (d, 2H, J=7.9 Hz, aromatic), 7.63 (d, 2H, J=8.3 Hz, aromatic), 7.97 (d, 1H, J=8.6 Hz, —NH—).

Example 27

Using ethyl (2s,3s)-3-[[[[(1s)-1-[[4-(2-chlorophenyl)-1-piperazinyl]carbonyl]-3-methyl]butyl]amino]carbonyl] oxiranecarboxylate in lieu of ethyl (2s,3s)-3-[[[[(1s)-1-[[4-(4-fluorophenyl)-1-piperazinyl]carbonyl]-2-phenyl]ethyl] amino]carbonyl]oxiranecarboxylate, the procedure of Example 21 was otherwise repeated to provide (2s,3s)-3-[[[[(1s)-1-[[4-(2-chlorophenyl)-1-piperazinyl]carbonyl]3-methyl]butyl]amino]carbonyl]oxiranecarboxylic acid (0.41 g, 67.2%).

$^1$H NMR (CDCl$_3$) δ: 0.97 (d, 3H, J=6.9 Hz, —C—CH$_3$), 0.98 (d, 3H, J=7.3 Hz, —C—CH$_3$), 1.38–1.47 (m, 1H, —C—CH—C$_2$), 1.65–1.77 (m, 2H, —C—CH$_2$—C—), 2.98–3.19 (m, 4H, piperazine ring), 3.55 (d, 1H, J=1.7 Hz, epoxy ring), 3.61–3.77 (m, 2H, piperazine ring), 3.64 (d, 1H, J=1.7 Hz, epoxy ring), 3.77–3.89 (m, 1H, piperazine ring), 3.89–4.15 (m, 1H, piperazine ring), 5.04–5.18 (m, 1H, —N—CH—CO), 7.00–7.06 (m, 2H, aromatic), 7.21–7.28 (m, 1H, aromatic), 7.37–7.41 (m, 1H, aromatic), 8.25 (d, 1H, J=8.9 Hz, —NH—).

Example 28

Using ethyl (2s,3s)-3-[[[[(1s)-1-[[4-(3-chlorophenyl)-1-piperazinyl]carbonyl]-3-methyl]butyl]amino]carbonyl] oxiranecarboxylate in lieu of ethyl (2s,3s)-3-[[[[(1s)-1-[[4-(4-fluorophenyl)-1-piperazinyl]carbonyl]-2-phenyl]ethyl] amino]carbonyl]oxiranecarboxylate, the procedure of Example 21 was otherwise repeated to provide (2s,3s)-3-[[[[(1s)-1-[[4-(3-chlorophenyl)-1-piperazinyl]carbonyl]-3-methyl]butyl]amino]carbonyl]oxiranecarboxylic acid (0.39 g, 67.2%).

$^1$H NMR (CDCl$_3$) δ: 0.96 (d, 3H, J=6.6 Hz, —C—CH$_3$), 0.99 (d, 3H, J=6.6 Hz, —C—CH$_3$), 1.36–1.47 (m, 1H, —C—CH—C$_2$), 1.64–1.80 (m, 2H, —C—CH$_2$—C—), 3.18–3.36 (m, 4H, piperazine ring), 3.53 (d, 1H, J=1.7 Hz, epoxy ring), 3.60–3.92 (m, 4H, piperazine ring), 3.62 (d, 1H, J=1.7 Hz, epoxy ring), 5.04–5.12 (m, 1H, —N—CH—CO), 5.5–6.5 (br d, 1H, —COOH), 6.77–6.82 (m, 1H, aromatic), 6.88–6.90 (m, 2H, aromatic), 7.17–7.23 (m, 1H, aromatic), 8.21 (d, 1H, J=8.6 Hz, —NH—).

Example 29

Using ethyl (2s,3s)-3-[[[[(1s)-1-[[4-(4-chlorophenyl)-1-piperazinyl]carbonyl]-3-methyl]butyl]amino]carbonyl] oxiranecarboxylate in lieu of ethyl (2s,3s)-3-[[[[(1s)-1-[[4-(4-fluorophenyl)-1-piperazinyl]carbonyl]- 2-phenyl]ethyl] amino]carbonyl]oxiranecarboxylate, the procedure of Example 21 was otherwise repeated to provide (2s,3s)-3-[[[[(1s)-1-[[4-(4-chlorophenyl)-1-piperazinyl]carbonyl]-3-methyl]butyl]amino]carbonyl]oxiranecarboxylic acid (0.33 g, 63.4%).

$^1$H NMR (CDCl$_3$) δ: 0.96 (d, 3H, J=6.6 Hz, —C—CH$_3$), 0.99 (d, 3H, J=6.59 Hz, —C—CH$_3$), 1.36–1.47 (m, 1H, —C—CH—C$_2$), 1.64–1.80 (m, 2H, —C—CH$_2$—C—), 3.10–3.31 (m, 4H, piperazine ring), 3.54 (d, 1H, J=1.7 Hz, epoxy ring), 3.58–3.93 (m, 4H, piperazine ring), 3.62 (d, 1H, J=1.7 Hz, epoxy ring), 5.04–5.12 (m, 1H, —N—CH—CO), 4.8–6.5 (br d, 1H, —COOH), 6.82–6.88 (m, 2H, aromatic), 7.21–7.26 (m, 1H, aromatic), 8.18 (d, 1H, J=8.9 Hz, —NH—).

Example 30

Using ethyl (2s,3s)-3-[[[[(1s)-1-[[4-(4-methoxyphenyl)-1-piperazinyl]carbonyl]-3-methyl]butyl]amino]carbonyl] oxiranecarboxylate in lieu of ethyl (2s,3s)-3-[[[[(1s)-1-[[4-(4-fluorophenyl)-1-piperazinyl]carbonyl]-2-phenyl]ethyl] amino]carbonyl]oxiranecarboxylate, the procedure of Example 21 was otherwise repeated to provide (2s,3s)-3-[[[[(1s)-1-[[4-(4-methoxyphenyl)-1-piperazinyl]carbonyl]-3-methyl]butyl]amino]carbonyl]oxiranecarboxylic acid (0.49 g, 56.7%).

$^1$H NMR (CDCl$_3$) δ: 0.95 (d, 3H, J=6.3 Hz, —C—CH$_3$), 0.99 (d, 3H, J=6.6 Hz, —C—CH$_3$), 1.38–1.46 (m, 1H, —C—CH—C$_2$), 1.63–1.80 (m, 2H, —C—CH$_2$—C—), 3.05–3.19 (m, 4H, piperazine ring), 3.55 (d, 1H, J=1.7 Hz, epoxy ring), 3.60–3.90 (m, 4H, piperazine ring), 3.62 (d, 1H, J=1.7 Hz, epoxy ring), 5.06–5.13 (m, 1H, —N—CH—CO), 4.8–5.8 (br d, 1H, —COOH), 6.84–7.00 (m, 4H, aromatic), 8.14 (d, 1H, J=8.6 Hz, —NH—).

Example 31

Using ethyl (2s,3s)-3-[[[[(1s)-1-[[4-(2-chlorophenyl)-1-piperazinyl]carbonyl]-2-methyl]propyl]amino]carbonyl] oxiranecarboxylate in lieu of ethyl (2s,3s)-3-[[[[(1s)-1-[[4-(4-fluorophenyl)-1-piperazinyl]carbonyl]-2-phenyl]ethyl] amino]carbonyl]oxiranecarboxylate, the procedure of Example 21 was otherwise repeated to provide (2s,3s)-3-[[[[(1s)-1-[[4-(2-chlorophenyl)-1-piperazinyl]carbonyl]-2-methyl]propyl]amino]carbonyl]oxiranecarboxylic acid (1.09 g, 89.5%) as colorless crystals.

$^1$H NMR (CDCl$_3$) δ: 0.98 (d, 3H, J=6.6 Hz, —C—CH$_3$), 1.01 (d, 3H, J=6.6 Hz, —C—CH$_3$), 2.10 (m, 1H, —CH—C$_2$), 2.98–3.14 (m, 4H, piperazine ring), 3.64 (d, J=1.6 Hz, 1H, epoxy ring), 3.66 (d, 1H, J=1.6 Hz, epoxy ring), 3.68–4.01 (m, 4H, piperazine ring), 4.98 (dd, 1H, J=8.9, 5.9 Hz, —N—CH—CO), 7.00–7.06 (m, 2H, aromatic), 7.24 (m, 1H, aromatic), 7.39 (m, 1H, aromatic), and 8.29 (d, 1H, J=8.9 Hz, —NH).

Example 32

Using ethyl (2s,3s)-3-[[[[[4-(2-chlorophenyl)-1-piperazinyl]carbonyl]methyl]amino]carbonyl] oxiranecarboxylate in lieu of ethyl (2s,3s)-3-[[[[(1s)-1-[[4-(4-fluorophenyl)-1-piperazinyl]carbonyl]-2-phenyl]ethyl] amino]carbonyl]oxiranecarboxylate, the procedure of Example 21 was otherwise repeated to provide (2s,3s)-3-[[[[[4-(2-chlorophenyl)-1-piperazinyl]carbonyl]methyl] amino]carbonyl]oxiranecarboxylic acid (1.08 g, 66.5%) as colorless crystals.

$^1$H NMR (CDCl$_3$) δ: 3.02–3.09 (m, 4H, piperazine ring), 3.63 (m, 2H, piperazine ring), 3.66 (d, 1H, J=1.6 Hz, epoxy ring), 3.78 (d, 1H, J=1.6 Hz, epoxy ring), 3.80 (m, 2H, piperazine ring), 4.11 (dd, 1H, J=17.0, 5.4 Hz, —N—CH—CO), 4.33 (dd, 1H, J=17.0, 5.4 Hz, —N—CH—CO), 6.99–7.05 (m, 2H, aromatic), 7.23 (m, 1H, aromatic), 7.38 (m, 1H, aromatic), and 8.67 (br d, 1H, —NH).

Example 33

Using ethyl (2s,3s)-3-[[[(1s)-1-[[4-(2-chlorophenyl)-1-piperazinyl]carbonyl]ethyl]amino]carbonyl] oxiranecarboxylate in lieu of ethyl (2s,3s)-3-[[[[(1s)-1-[[4-(4-fluorophenyl)-1-piperazinyl]carbonyl]-2-phenyl]ethyl] amino]carbonyl]oxiranecarboxylate, the procedure of Example 21 was otherwise repeated to provide (2s,3s)-3-[[[(1s)-1-[[4-(2-chlorophenyl)-1-piperazinyl]carbonyl] ethyl]amino]carbonyl]oxiranecarboxylic acid (0.87 g, 77.5%) as colorless crystals.

¹H NMR (CDCl₃) δ: 1.41 (d, 3H, J=6.8 Hz, —C—CH₃), 2.98–3.13 (m, 4H, piperazine ring), 3.61 (d, 1H, J=1.6 Hz, epoxy ring), 3.63 (d, 1H, J=1.6 Hz, epoxy ring), 3.67–3.84 (m, 3H, piperazine ring), 3.95 (m, 1H, piperazine ring), 5.06 (dq, 1H, J=8.4, 6.8 Hz, —N—CH—CO), 7.00–7.06 (m, 2H, aromatic), 7.24 (m, 1H, aromatic), 7.39 (m, 1H, aromatic), and 8.13 (d, 1H, J=8.4, —NH).

Example 34

Using ethyl (2s,3s)-3-[[[[(1s)-1-[[4-(2-chlorophenyl)-1-piperazinyl]carbonyl]-2-methyl]butyl]amino]carbonyl] oxiranecarboxylate in lieu of ethyl (2s,3s)-3-[[[[(1s)-1-[[4-(4-fluorophenyl)-1-piperazinyl]carbonyl]-2-phenyl]ethyl]amino]carbonyl]oxiranecarboxylate, the procedure or Example 21 was otherwise repeated to provide (2s,3s)-3-[[[[(1s)-1-[[4-(2-chlorophenyl)-1-piperazinyl]carbonyl]-2-methyl]butyl]amino]carbonyl]oxiranecarboxylic acid (1.07 g, 77.4%) as colorless crystals.

¹H NMR (CDCl₃) δ: 0.92 (t, 3H, J=7.3 Hz, —C—CH₃), 1.00 (d, 3H, J=6.8 Hz, —C—CH₃), 1.22 (m, 1H, —CH—C₂—) 1.54 (m, 1H, —CH—C), 1.84 (m, 1H, —CH—C), 2.97–3.17 (m, 4H, piperazine ring), 3.60 (d, 1H, J=1.6 Hz, epoxy ring), 3.64 (d, 1H, J=1.6 Hz, epoxy ring), 3.65–3.79 (m, 2H, piperazine ring), 3.85–4.05 (m, 2H, piperazine ring), 4.98 (dd, 1H, J=9.2, 6.3 Hz, —N—CH—CO), 7.00–7.06 (m, 2H, aromatic), 7.24 (m, 1H, aromatic), 7.39 (m, 1H, aromatic), and 8.29 (d, 1H, J=9.2 Hz, —NH).

Example 35

Using ethyl (2s,3s)-3-[[[2-[[4-(2-chlorophenyl)-1-piperazinyl]carbonyl]ethyl]amino]carbonyl] oxiranecarboxylate in lieu of ethyl (2s,3s)-3-[[[[(1s)-1-[[4-(4-fluorophenyl)-1-piperazinyl]carbonyl]-2-phenyl]ethyl]amino]carbonyl]oxiranecarboxylate, the procedure of Example 21 was otherwise repeated to provide (2s,3s)-3-[[[2-[[4-(2-chlorophenyl)-1-piperazinyl]carbonyl]ethyl]amino]carbonyl]oxiranecarboxylic acid (0.85 g, 78.9%) as colorless crystals.

¹H NMR (DMSO-d₆) δ: 2.56 (t, 2H, J=6.9 Hz, —C—CH₂—CO), 2.91–2.98 (m, 4H, piperazine ring), 3.35 (td, 2H, J=6.9, 5.6 Hz, N—CH₂—C), 3.49 (d, 1H, J=2.0 Hz, epoxy ring), 3.59 (d, 1H, J=1.6 Hz, epoxy ring), 3.56–3.64 (m, 2H, piperazine ring), 3.80 (m, 2H, piperazine ring), 7.07 (td, 1H, J=7.9, 1.7 Hz, aromatic), 7.15 (dd, 1H, J=7.9, 1.7 Hz, aromatic), 7.43 (dd, 1H, J=7.9, 1.7 Hz, aromatic), 7.31 (m, 1H, aromatic), 8.40 (t, 1H, J=5.6 Hz, —NH), and 13.50 (br d, 1H, —COOH).

Example 36

Using ethyl (2s,3s)-3-[[[[N-[[4-(2-chlorophenyl)-1-piperazinyl]carbonyl]methyl]-N-methyl]amino]carbonyl] oxiranecarboxylate in lieu of ethyl (2s,3s)-3-[[[[(1s)-1-[[4-(4-fluorophenyl)-1-piperazinyl]carbonyl]-2-phenyl]ethyl]amino]carbonyl]oxiranecarboxylate, the procedure of Example 21 was otherwise repeated to provide (2s,3s)-3-[[[[N-[[4-(2-chlorophenyl)-1-piperazinyl]carbonyl]methyl] N-methyl]amino]carbonyl]oxiranecarboxylic acid (1.08 g, 74.8%) as colorless crystals.

¹H NMR (CDCl₃) δ: 3.01–3.10 (m, 6H, piperazine ring), 3.27 (s, 3H, —NCH₃), 3.63–3.71 (m, 2H, —N—CH₂—CO), 3.75 (d, 1H, J=1.9 Hz, epoxy ring), 3.78–3.90 (m, 2H, piperazine ring), 4.02 (d, 1H, J=1.9 Hz, epoxy ring), 6.98–7.05 (m, 2H, aromatic), 7.24 (m, 1H, aromatic), and 7.36 (m, 1H, aromatic).

Example 37

Using ethyl (2s,3s)-3-[[(2s)-2-[[4-(2-chlorophenyl)-1-piperazinyl]carbonyl]-1-pyrrolidinyl]carbonyl] oxiranecarboxylate in lieu of ethyl (2s,3s)-3-[[[[(1s)-1-[[4-(4-fluorophenyl)-1-piperazinyl]carbonyl]-2-phenyl]ethyl]amino]carbonyl]oxiranecarboxylate, the procedure of Example 21 was otherwise repeated to provide (2s,3s)-3-[[(2s)-2-[[4-(2-chlorophenyl)-1-piperazinyl]carbonyl]-1-pyrrolidinyl]carbonyl]oxiranecarboxylic acid (0.94 g, 7.07%) as colorless crystals.

¹H NMR (CDCl₃) δ: 1.94–2.11 (m, 2H, pyrrolidine ring), 2.17–2.30 (m, 2H, pyrrolidine ring), 3.06–3.20 (m, 4H, piperazine ring), 3.63–3.76 (m, 2H, piperazine ring), 3.81–3.85 (m, 5H), 4.00 (dt, 1H, J=13.7, 4.4 Hz, pyrrolidine ring), 4.96 (dd, 1H, J=7.8, 4.3 Hz, pyrrolidine ring), 6.97–7.04 (m, 2H, aromatic), 7.24 (m, 1H, aromatic), and 7.37 (m, 1H, aromatic).

Example 38

Using ethyl (2s,3s)-3-[[[[(1s)-1-[[4-(2-chlorophenyl)-1-piperazinyl]carbonyl]-2-acetylaminomethylthio]ethyl]amino]carbonyl]oxiranecarboxylate in lieu of ethyl (2s,3s)-3-[[[[(1s)-1-[[4-(4-fluorophenyl)-1-piperazinyl]carbonyl]-2-phenyl]ethyl]amino]carbonyl]oxiranecarboxylate, the procedure of Example 21 was otherwise repeated to provide (2s,3s)-3-[[[[(1s)-1-[[4-(2-chlorophenyl)-1-piperazinyl]carbonyl]-2-acetylaminomethylthio]ethyl]amino]carbonyl]oxiranecarboxylic acid (0.88 g, 77.9%) as colorless crystals.

¹H NMR (CDCl₃) δ: 2.05 (s, 3H, —COCH₃), 2.85 (dd, 1H, J=13.9, 8.3 Hz, —C—CH—S), 2.96–3.16 (m, 5H), 3.69 (d, 1H, J=1.6 Hz, epoxy ring), 3.78 (d, 1H, J=1.6 Hz, epoxy ring), 3.71–3.89 (m, 4H, piperazine ring), 4.39 (d, 2H, J=8.3 Hz, —S—CH₂—N), 5.21 (m, 1H, —N—CH—CO), 6.97–7.02 (m, 2H, aromatic), 7.22 (m, 1H, aromatic), 7.36 (m, 1H, aromatic), 7.80 (d, 1H, J=8.3, —NH), and 9.00 (br d, 1H, —NH).

Example 39

Using ethyl (2s,3s)-3-[[[[(1s)-1-[[4-(2-chlorophenyl)-1-piperazinyl]carbonyl]-3-methylthio]propyl]amino]carbonyl]oxiranecarboxylate in lieu of ethyl (2s,3s)-3-[[[[(1s)-1-[[4-(4-fluorophenyl)-1-piperazinyl]carbonyl]-2-phenyl]ethyl]amino]carbonyl]oxiranecarboxylate, the procedure of Example 21 was otherwise repeated to provide (2s,3s)-3-[[[[(1s)-1-[[4-(2-chlorophenyl)-1-piperazinyl]carbonyl]-3-methylthio]propyl]amino]carbonyl]oxiranecarboxylic acid (1.17 g, 80.7%) as colorless crystals.

¹H NMR (CDCl₃) δ: 1.98 (dd, 2H, J=6.9, 6.6 Hz, —CH—C—C), 2.12 (s, 3H, —SCH₃), 2.57 (dt, 2H, J=6.9, 2.3 Hz, —C—CH₂—C—S), 3.05–3.19 (m, 4H, piperazine ring), 3.63 (d, 1H, J=1.9 Hz, epoxy ring), 3.65 (d, 1H, J=1.9 Hz, epoxy ring), 3.71–3.94 (m, 4H, piperazine ring), 5.26 (m, 1H, —N—CH—CO), 7.00–7.06 (m, 2H, aromatic), 7.24 (m, 1H, aromatic), 7.38 (m, 1H, aromatic), and 8.18 (d, 1H, J=8.6, —NH).

Example 40

Using ethyl (2s,3s)-3-[[[[(1s)-1-[[4-(2-chlorophenyl)-1-piperazinyl]carbonyl]-3-carbamoyl]propyl]amino]carbonyl] oxiranecarboxylate in lieu of ethyl (2s,3s)- 3-[[[[(1s)-1-[[4-(4-fluorophenyl)-1-piperazinyl]carbonyl]-2-phenyl]ethyl]amino]carbonyl]oxiranecarboxylate, the procedure of Example 21 was otherwise repeated to provide (2s,3s)-3-[[[[(1s)-1-[[4-(2-chlorophenyl)-1-piperazinyl]carbonyl]-3-carbamoyl]propyl]amino]carbonyl]oxiranecarboxylic acid (0.14 g, 74.5%) as colorless crystals.

¹H NMR (CDCl₃) δ: 1.85 (br d, 2H, —NH₂), 2.14 (m, 1H, —C—CH—C—CO—), 2.36–2.53 (m, 3H, —CH—CH₂—

C—CO—), 2.89–3.06 (m, 4H, piperazine ring), 3.57–3.79 (m, 6H, piperazine and epoxy ring), 5.02 (m, 1H, —N—CH—CO), 6.96–7.02 (m, 2H, aromatic), 7.21 (m, 1H, aromatic), 7.37 (m, 1H, aromatic), and 7.88 (br d, 1H, —NH).

Example 41

Using ethyl (2s,3s)-3-[[[(1s)-1-[[4-(4-fluorophenyl)-1-piperazinyl]carbonyl]-1-cyclopentyl]amino]carbonyl] oxiranecarboxylate in lieu of ethyl (2s,3s)-3-[[[[(1s)-1-[[4-(4-fluorophenyl)-1-piperazinyl]carbonyl]-2-phenyl]ethyl] amino]carbonyl]oxiranecarboxylate, the procedure of Example 21 was otherwise repeated to provide (2s,3s)-3-[[[(1s)-1-[[4-(4-fluorophenyl)-1-piperazinyl]carbonyl]-1-cyclopentyl]amino]carbonyl]oxiranecarboxylic acid (0.52 g, 55.6%) as colorless crystals.

$^1$H NMR (DMSO-$d_6$) δ: 1.61 (m, 4H, cyclopentyl), 1.87 (m, 2H, cyclopentyl), 2.22 (m, 2H, cyclopentyl), 2.97 (m, 4H, piperazine), 3.45 (d, 1H, J=1.6 Hz, epoxy ring), 3.58 (d, 1H, J=2.1 Hz, epoxy ring), 3.60 (m, 4H, piperazine ring), 6.95–7.20 (m, 4H, aromatic), 8.89 (s, 1H, —NH) and 13.4 (br d, 1H, —COOH).

Example 42

To a solution of the (2s,3s)-3-[[[[(1s)-1-[[4-(4-methylphenylsulfonyl)-1-piperazinyl]carbonyl]-3-methyl] butyl]amino]carbonyl]oxiranecarboxylic acid (0.935 g, 2 mmol) obtained in Example 26 in dichloromethane (15 ml) were added o-benzylhydroxylamine (0.638 g, 4.0 mmol) and N-methylmorpholine (0.405 g, 4.0 mmol). Then, a solution of dicyclohexylcarbodiimide (0.619 g, 3.0 mmol) in dichloromethane (5 ml) was added dropwise under ice-cooling. The mixture was stirred at room temperature for 24 hours, at the end of which time it was filtered. The precipitate was washed with dichloromethane (20 ml) and the washes and the filtrate were pooled and washed with water. The organic layer was dried over anhydrous magnesium sulfate and concentrated under reduced pressure and the residue was chromatographed on silica gel. Elution was carried out with ethyl acetate-hexane (2:1) to provide (2s,3s)-3-[[[[(1s)-1-[[4-(4-methylphenylsulfonyl)-1-piperazinyl]carbonyl]-3-methyl]butyl]amino]carbonyl]oxiranecarbobenzyloxamide (0.86 g, 75.1%).

$^1$H NMR (CDCl$_3$) δ: 0.84 (d, 3H, J=6.2 Hz, —C—CH$_3$), 0.91 (d, 3H, J=6.5 Hz, —C—CH$_3$), 1.23–1.31 (m, 1H, —C—CH$_2$—C), 1.36–1.58 (m, 2H, —C—CH—C, —C—CH—C$_2$), 2.43 (s, 3H, —ph—CH$_3$), 2.72–2.86 (m, 2H, piperazine ring), 3.14–3.27 (m, 2H, piperazine ring), 3.31–3.51 (m, 2H, piperazine ring), 3.40 (d, 1H, J=1.4 Hz, epoxy ring), 3.43 (d, 1H, J=1.7 Hz, epoxy ring), 3.63–3.74 (m, 1H, piperazine ring), 3.84–3.98 (m, 1H, piperazine ring), 4.80–4.90 (m, 1H, —N—CH—CO), 4.87 (s, 3H, —O—CH$_2$—ph), 7.30–7.40 (m, 8H, aromatic, —NH—), 7.56–7.66 (m, 2H, aromatic), 9.05 (s, 1H, —NH—).

Example 43

To a solution of the (2s,3s)-3-[[[[(1s)-1-[[4-(4-methylphenylsulfonyl)-1-piperazinyl]carbonyl]-3-methyl] butyl]amino]carbonyl]oxiranecarbobenzyloxamide (0.57 g, 1 mmol) obtained in Example 42 in methanol (25 ml) was added a catalyst amount of palladium-on-carbon and catalytic reduction was carried out. After completion of the reaction, the palladium-on-carbon was filtered off and the filtrate was concentrated and chromatographed on silica gel. Elution was carried out with ethyl acetate to provide (2s, 3s)-3-[[[[(1s)-1-[[4-(4-methylphenylsulfonyl)-1-piperazinyl]carbonyl]-3-methyl]butyl]amino]carbonyl] oxiranecarbohydroxami c acid (0.18 g, 37.3%).

$^1$H NMR (CDCl$_3$) δ: 0.84 (d, 3H, J=5.9 Hz, —C—CH$_3$), 0.90 (d, 3H, J=5.9 Hz, —C—CH$_3$), 1.24–1.33 (m, 1H, —C—CH$_2$—C), 1.50–1.64 (m, 2H, —C—CH—C, —C—CH—C$_2$), 2.42 (s, 3H, —ph—CH$_3$), 2.90–3.20 (m, 4H, piperazine ring), 3.44–3.80 (m, 3H, piperazine ring), 3.51 (s, 1H, epoxy ring), 3.68 (s, 1H, epoxy ring), 4.56–4.66 (m, 1H, piperazine ring), 4.76–4.90 (m, 1H, —N—CH—CO), 7.33 (d, 2H, J=7.8 Hz, aromatic), 7.62 (dd, 2H, J=7.8, 1.7 Hz, aromatic), 7.84–7.94 (br d, 1H, —NH—), 9.80–10.40 (br d, 1H, —OH).

Formulation Example 1

Tablets

Compound of Example 30 80 mg
Starch 17 mg
Magnesium stearate 3 mg

The above components per tablet are compressed into tablets in the routine manner. Where necessary, the tablets can be sugar-coated.

Formulation Example 2

Capsules

Compound of Example 25 50 mg
Lactose 100 mg
Starch 30 mg
Magnesium stearate 10 mg The above components per tablet are mixed and filled in gelatin capsule shells.

Formulation Example 3

Injection

Compound of Example 28 2.5 mg
Sodium chloride 900 mg
1N-sodium hydroxide q.s.
Distilled water for injection to make 100 ml The above components are mixed in the routine manner to provide an injection.

Formulation Example 4

Ophthalmic solution

Compound of Example 25 50 mg
Boric acid 700 mg
Borax q.s.
Sodium chloride 500 mg
Sodium edetate 0.05 mg
Benzalkonium chloride 0.005 mg
Sterilized pure water to make 100 ml The above components are mixed in the routine manner to provide an ophthalmic solution.

EFFECT OF THE INVENTION

The compound of general formula (I) according to the present invention has cysteine protease inhibitory activity and is, therefore, can be used as a therapeutic drug for myodystrophy, amyotrophy, cerebral infarction, stroke (cerebral apoplexy), Alzheimer's disease, disturbance of consciousness or dyskinesia associated with head trauma, multiple sclerosis, peripheral neuropathy, cataract, inflammation, allergy, fulminanthepatitis, osteoporosis, hypercalcemia, breast cancer, prostate cancer, prostatic hypertrophy, etc. or a cancer growth inhibitor or antimetastatic agent, or a platelet aggregation inhibitor.

What is claimed is:

1. A compound of the following formula (I) or its salt,

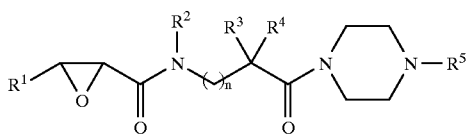
(I)

wherein $R^1$ represents either carboxy which may be esterified with $C_{1-6}$ alkoxy, or amidated carboxy which may be substituted with hydroxy, alkoxy or benzyloxy; $R^2$ represents hydrogen or lower alkyl and may be linked to $R^3$ or $R^4$ to form a pyrrolidine ring; $R^3$ and $R^4$ may be the same or different and each represents hydrogen, lower alkyl which may be substituted by a benzene ring, an indole ring or carbamoyl, or $C_{1-4}$ alkyl-thio-$C_{1-4}$ alkyl which may be substituted by formylamino, acetylamino, propionylamino, butyrylamino, isobutyrylamino, valerylamino, isovalerylamino, pivaloylamino or n-hexanoylamino, and $R^3$ and $R^4$ may conjoinedly form a cyclopropane, cyclobutane, cyclopentane, cyclohexane or cycloheptane ring; $R^5$ represents a substituted phenyl group of formula (II)

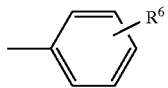
(II)

(wherein $R^6$ represents halogen or alkoxy) or a substituted sulfonyl group of formula (III)

$$-SO_2-R^7 \qquad (III)$$

(wherein $R^7$ represents either phenyl or naphthyl which may be substituted by lower alkyl, or amino which may be substituted by $C_{1-6}$ straight-chain, branched-chain or cyclic alkyl); and n is 0 or 1.

2. The compound or salt according to claim 1 wherein $R^2$ is hydrogen or methyl.

3. The compound or salt according to claim 1 wherein $R^3$ and $R^4$ may be the same or different and each is hydrogen, lower alkyl which may be substituted by an a benzene or carbamoyl, or $C_{1-4}$ alkyl-thio-$C_{1-4}$ alkyl which may be substituted by acetylamino.

4. The compound or salt according to claim 1 wherein the ring formed conjoinedly by $R^3$ and $R^4$ is cyclopentane.

5. The compound or salt according to claim 1 wherein $R^6$ in formula (II) representing substituted phenyl is chlorine or fluorine.

6. The compound or salt according to claim 1 wherein $R^7$ in formula (III) representing substituted sulfonyl is either phenyl which may be substituted by lower alkyl or dimethylamino.

7. A pharmaceutical composition comprising the compound or salt of claim 1 as an active ingredient.

8. A cysteine protease inhibitor composition comprising 0.1–500 mg of the compound or salt of claim 1 as an active ingredient.

9. A calpain inhibitor composition comprising 1–200 mg of the compound or salt of claim 1 as an active ingredient.

* * * * *